US012778537B2

(12) United States Patent
Yang et al.

(10) Patent No.: US 12,778,537 B2
(45) Date of Patent: Nov. 3, 2026

(54) SYSTEM FOR AUTOMATED REAL-TIME DETECTION, OUTLINING, TRACKING AND CHARACTERIZATION OF BLOOD VESSELS IN ULTRASOUND IMAGING

(71) Applicant: Exo Imaging, Inc., Santa Clara, CA (US)

(72) Inventors: Yongyi Yang, Westmont, IL (US); Miles N. Wernick, Evanston, IL (US); Jonathan A. Bowman, Montgomery, AL (US)

(73) Assignee: Exo Imaging, Inc., Santa Clara, CA (US)

( * ) Notice: Subject to any disclaimer, the term of this patent is extended or adjusted under 35 U.S.C. 154(b) by 301 days.

(21) Appl. No.: 18/683,702

(22) PCT Filed: Aug. 27, 2021

(86) PCT No.: PCT/US2021/048051
§ 371 (c)(1),
(2) Date: Feb. 14, 2024

(87) PCT Pub. No.: WO2023/027733
PCT Pub. Date: Mar. 2, 2023

(65) Prior Publication Data

US 2024/0374233 A1 Nov. 14, 2024

(51) Int. Cl.
*A61B 8/06* (2006.01)
*A61B 8/00* (2006.01)
(Continued)

(52) U.S. Cl.
CPC ................ *A61B 8/06* (2013.01); *A61B 8/085* (2013.01); *A61B 8/14* (2013.01); *A61B 8/463* (2013.01); *A61B 8/488* (2013.01)

(58) Field of Classification Search
CPC ........... A61B 8/06; A61B 8/085; A61B 8/488; A61B 8/5223
See application file for complete search history.

(56) References Cited

U.S. PATENT DOCUMENTS 5,908,391 A 6/1999 Muzilla et al.
2004/0242987 A1* 12/2004 Liew ...................... G16H 50/30 600/407
(Continued)

FOREIGN PATENT DOCUMENTS

CA 3152545 A1 3/2021
JP 2014221175 B 11/2013
(Continued)

OTHER PUBLICATIONS

EPO European Extended Search Report in EP Application Serial No. 21955242.9 mailed on Apr. 3, 2025, 8 pages.
(Continued)

*Primary Examiner* — Rochelle D Turchen
(74) *Attorney, Agent, or Firm* — Alliance IP, LLC

(57) ABSTRACT

An apparatus, a method, and computer-implemented media. The apparatus is to perform a vessel detection algorithm to detect, in real time during image generation by an ultrasound imaging device, a vessel of a living body, the algorithm including: determining current vessel parameters based on a current ultrasonic image frame on a display at a current time; determining preceding vessel parameters based on a preceding ultrasonic image frame on the display at a time preceding the current time; determining current flow data for vessel fluid flow corresponding to the current ultrasonic image frame; and detecting and tracking the vessel based on the current vessel parameters, the preceding vessel parameters and the current flow data; and determine and cause to display to a user, via a user interface device that includes the display,
(Continued)

information regarding a suitability of the vessel for access by a predetermined foreign object.

22 Claims, 6 Drawing Sheets

(51) Int. Cl.
*A61B 8/08* (2006.01)
*A61B 8/14* (2006.01)

(56) References Cited

U.S. PATENT DOCUMENTS

| | | | |
|---|---|---|---|
| 2006/0098853 | A1 | 5/2006 | Roundhill et al. |
| 2012/0078106 | A1 | 3/2012 | Dentinger et al. |
| 2013/0345566 | A1 | 12/2013 | Weitzel et al. |
| 2018/0014810 | A1 | 1/2018 | Chen et al. |
| 2019/0099108 | A1 | 4/2019 | Messerly et al. |
| 2019/0099145 | A1 | 4/2019 | Kim |
| 2019/0239848 | A1 | 8/2019 | Bedi et al. |
| 2021/0045710 | A1 | 2/2021 | Bedi et al. |
| 2021/0315538 | A1* | 10/2021 | Brandl .................. G16H 70/20 |
| 2022/0172354 | A1* | 6/2022 | Misener .................. A61B 8/06 |

FOREIGN PATENT DOCUMENTS

| | | | |
|---|---|---|---|
| KR | 20020041577 | A | 6/2002 |
| WO | 2020044769 | A1 | 3/2020 |

OTHER PUBLICATIONS

PCT International Search Report and Written Opinion issued in PCT/US2021/048051, dated May 26, 2022; 14 pages.

KIPO Preliminary Rejection issued in Application No. 10-2024-7009504, mailed Apr. 20, 2026; with English Machine Translation 24 pages.

* cited by examiner

SYSTEM FOR AUTOMATED REAL-TIME DETECTION, OUTLINING, TRACKING AND CHARACTERIZATION OF BLOOD VESSELS IN ULTRASOUND IMAGING

CROSS REFERENCE TO RELATED APPLICATION

This Application is a national phase filing under 35 U.S.C. § 371 of International Patent Application Serial No. PCT/US2021/048051, filed Aug. 27, 2021, and entitled, "SYSTEM FOR AUTOMATED REAL-TIME DETECTION, OUTLINING, TRACKING AND CHARACTERIZATION OF BLOOD VESSELS IN ULTRASOUND IMAGING," the entire disclosure of which is incorporated herein by reference.

BACKGROUND

Field

Embodiments relate in general to the field of signal processing for imaging devices, and in particular to the field of signal processing for ultrasound imaging devices or probes such as ones including micromachined ultrasound transducers (MUTs).

Background

Ultrasound imaging is widely used in the fields of medicine and non-destructive testing.

An ultrasound imaging probe or ultrasonic imaging device typically includes an array of many individual ultrasonic transducers (pixels) that are used to emit and receive acoustic energy relative to a target to be imaged. A reflected waveform is received by a transducer (for example, a micro-machined ultrasonic transducer), converted to an electrical signal and, with further signal processing, an image is created. Fluid velocity and direction of fluid flow (for example, with respect to blood flow) may also be measured or detected by ultrasound and presented visually to the ultrasound imaging device operator. This quantification and visualization of anatomical structures and movement can be utilized in support of a range of medical diagnostic applications and other medical procedures.

Among the most common medical procedures is vascular access including procedures involving the placement of intravenous catheters, including peripherally inserted central catheters (PICC), central venous catheters (CVC), and peripheral intravenous (PIV) catheters.

However, catheter placement, which involves insertion of a needle, may be difficult, and may require multiple attempts. Each extra attempt can cause unnecessary pain, injury, and health risks for the patient, while creating added labor and materials costs for the healthcare institution. When an artery is inadvertently struck by a needle, significant and potentially dangerous bleeding can occur. When a nerve is inadvertently struck by a needle, it can cause unnecessary pain for the patient.

SUMMARY

The ultrasonic imaging device of some embodiments may operate according to one or more sets of instructions, including algorithms, which may be used collectively or individually, to assist a user of an ultrasound imaging device to identify human or animal anatomical features such as veins, arteries and nerves, such as for the purpose of guiding the placement of intravenous catheters.

BRIEF DESCRIPTION OF THE DRAWINGS

The novel features of the invention are set forth with particularity in the appended claims. A better understanding of the features and advantages of Some embodiments will be obtained by reference to the following detailed description that sets forth illustrative embodiments, in which the principles of the invention are utilized, and the accompanying drawings (also "FIGURE" and "FIG." herein), of which:

DETAILED DESCRIPTION

Figure 1:
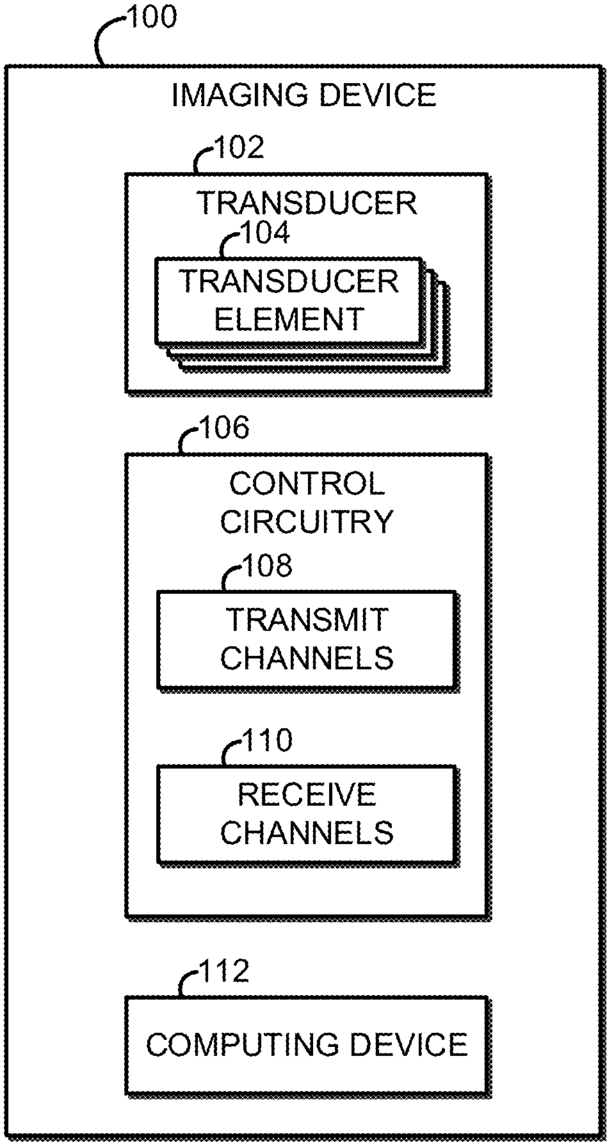
FIG. 1 is a block diagram of an imaging device with selectively alterable characteristics, in accordance with disclosed embodiments.

Some embodiments relate to imaging devices, and more particularly to ultrasound imaging devices that are electronically configurable. Ultrasound imaging devices may be used to image internal tissue, bones, blood flow, or organs of human or animal bodies in a non-invasive manner. The images can then be displayed. To perform ultrasound imaging, the ultrasound imaging devices transmits an ultrasonic signal into the body and receive a reflected signal from the body part being imaged. Such ultrasound imaging devices include transducers and associated electronics, which may be referred to as transceivers or imagers, and which may be based on photo-acoustic or ultrasonic effects. Such transducers may be used for imaging and may be used in other applications as well. For example, the transducers may be used in medical imaging; flow measurements in pipes, speaker, and microphone arrays; lithotripsy; localized tissue heating for therapeutic; and highly intensive focused ultrasound (HIFU) surgery.

Additional aspects and advantages of some embodiments will become readily apparent to those skilled in this art from the instant detailed description, wherein only illustrative embodiments are shown and described. As will be realized, some embodiments are capable of achieving other, different goals, and their several details are capable of modifications in various obvious respects, all without departing from the disclosure. Accordingly, the drawings and description are to be regarded as illustrative in nature, and not as restrictive.

Ultrasound imaging is being used increasingly to improve outcomes in vascular access by providing direct visualization of vessels and nerves before and during needle insertion. The human interpretation of ultrasound imaging is challenging for the clinical practitioner (i.e. clinical human practitioner) due to the difficulty of interpretation of the images by a human operator. Therefore, the use of ultrasound for catheter placement has been limited mainly to the more-demanding task of placing central lines (PICC and CVC), which is often done by specialists, whereas the more routine PIV performed by nurses are usually done without the benefit of ultrasound. However, even for experienced human practitioners, ultrasound image quality in some patients can make interpretation of such images for vein or artery identification unreliable.

Although the instant disclosure mentions vein detection/identification and vein tracking, it is to be understood and embodiments are not so limited, and include within their scope the identification of human or animal vessels that sustain fluid flow (hereafter, "flow vessel").

Once a vein is successfully found, the vein diameter must be measured, and an appropriate size of catheter must be determined. Vein diameter is typically measured in a semi-manual way by using hand-drawn "calipers" on the screen of the ultrasound imager. Appropriate catheter size is usually determined from the vein diameter by applying a formula or looking up the value in a table. These steps cost valuable time, which may be avoided by automating the process.

For all users, it is beneficial to confirm that the vessel chosen for access is truly a vein. It should also be demonstrated that the vein is compressible, to avoid accessing a vein affected by clotting.

Consequently, there exists a need to: 1) simplify the process of ultrasound-guided vascular access so that less-experienced practitioners can utilize the technique; 2) improve outcomes achieved by practitioners, even those who are already experienced with ultrasound imaging; 3) and shorten the time taken to complete the procedure.

Some embodiments fulfill these needs through the use of computerized algorithms for automatic interpretation of ultrasound images generated by ultrasonic imagers. The computerized algorithm of some embodiments are implemented in an ultrasound imaging system and performs identifying and delineating (outlining) or otherwise visually indicating veins and arteries; measuring and characterizing vessels; assessing a vein's suitability for access; and recommending of catheter gauge. A feature of some embodiments is their ability to be applied in real time during an insertion procedure involving an insertion of a foreign body in the vessel, allowing the practitioner to quickly identify vessels as they appear on screen, and to track these structures as the scan progresses.

In general, some embodiments relate to imaging devices, and more particularly to imaging devices having electronically configurable ultrasonic transducers. Non-intrusive imaging devices may be used to image internal tissue, bones, blood flow, or organs of human or animal bodies. The images can then be displayed. To perform the imaging, the imaging devices transmit a signal into the body and receive a reflected signal from the body part being imaged. Such imaging devices include transducers, which may be referred to as transceivers or imagers, and which may be based on photo-acoustic or ultrasonic effects. Such transducers may be used for imaging and may be used in other applications as well. For example, the transducers may be used in medical imaging; flow measurements in pipes, speaker, and microphone arrays; lithotripsy; localized tissue heating for therapeutic purposes; and highly intensive focused ultrasound (HIFU) surgery.

Traditionally, imaging devices such as ultrasound imagers used in medical imaging use piezoelectric (PZT) materials or other piezo ceramic and polymer composites. Such imaging devices may include a housing to house the transducers with the PZT material, as well as other electronics that form and display the image on a display unit. To fabricate the bulk PZT elements or the transducers, a thick piezoelectric material slab may be cut into large rectangular shaped PZT elements. These rectangular-shaped PZT elements may be expensive to build, since the manufacturing process involves precisely cutting generally the rectangular-shaped thick PZT or ceramic material and mounting it on substrates with precise spacing. Further, the impedance of the transducers is much higher than the impedance of the transmit/receive electronics for the transducers, which can affect performance.

Still further, such thick bulk PZT elements can require very high voltage pulses, for example 100 volts (V) or more to generate transmission signals. This high drive voltage results in high power dissipation, since the power dissipation in the transducers is proportional to the square of the drive voltage. This high power dissipation generate heat within the imaging device such that cooling arrangements are necessitated. These cooling systems increase the manufacturing costs and weights of the imaging devices which makes the imaging devices more burdensome to operate.

Even further, the transmit/receive electronics for the transducers may be located far away from the transducers themselves, thus requiring micro-coax cables between the transducers and transmit/receive electronics. In general, the cables have a precise length for delay and impedance matching, and, quite often, additional impedance matching networks are used for efficient connection of the transducers through the cables to the electronics.

Some embodiments may be utilized in the context of imaging devices that utilize either piezoelectric micromachined ultrasound transducer (pMUT) or capacitive micromachine ultrasonic transducer (cMUT) technologies, as described in further detail herein.

In general, MUTs, such as both cMUT and pMUT, include a diaphragm (a thin membrane attached at its edges, or at some point in the interior of the probe), whereas a "traditional," bulk PZT element typically consists of a solid piece of material.

Piezoelectric micromachined ultrasound transducers (pMUTs) may be efficiently formed on a substrate leveraging various semiconductor wafer manufacturing operations. Semiconductor wafers may currently come in 6 inch, 8 inch, and 12 inch sizes and are capable of housing hundreds of transducer arrays. These semiconductor wafers start as a silicon substrate on which various processing operations are performed. An example of such an operation is the formation of $SiO_2$ layers, also known as insulating oxides. Various other operations such as the addition of metal layers to serve as interconnects and bond pads are performed to allow connection to other electronics. Yet another example of a machine operation is the etching of cavities. Compared to the conventional transducers having bulky piezoelectric material, pMUT elements built on semiconductor substrates are less bulky, are cheaper to manufacture, and have simpler and higher performance interconnection between electronics and transducers. As such, they provide greater flexibility in the operational frequency of the imaging device using the same, and potential to generate higher quality images.

In some embodiments, the imaging device is coupled to an application specific integrated circuit (ASIC) that includes transmit drivers, sensing circuitry for received echo signals, and control circuitry to control various operations. The ASIC may be formed on another semiconductor wafer. This ASIC may be placed in close proximity to pMUT or cMUT elements to reduce parasitic losses. As a specific example, the ASIC may be 50 micrometers (μm) or less away from the transducer array. In a broader example, there may be less than 100 μm separation between the 2 wafers or 2 die, where each wafer includes many die and a die includes a transducer in the transducer wafer and an ASIC in the ASIC wafer. In some embodiments, the ASIC has matching dimensions relative to the pMUT or cMUT array and allows the devices to be stacked for wafer-to-wafer interconnection or transducer die on ASIC wafer or transducer die to ASIC die interconnection. Alternatively, the transducer can also be developed on top of the ASIC wafer using low temperature piezo material sputtering and other low temperature processing compatible with ASIC processing.

Wherever the ASIC and the transducer interconnect, according to one embodiment, the two may have similar footprints. More specifically, according to the latter embodiment, a footprint of the ASIC may be an integer multiple or divisor of the MUT footprint.

Regardless of whether the imaging device is based on pMUT or cMUT, an imaging device according to some embodiments may include a number of transmit channels and a number of receive channels. Transmit channels are to drive the transducer elements with a voltage pulse at a frequency the elements are responsive to. This causes an ultrasonic waveform to be emitted from the elements, which waveform is to be directed towards an object to be imaged, such as toward an organ in a body. In some examples, the imaging device with the array of transducer elements may make mechanical contact with the body using a gel in between the imaging device and the body. The ultrasonic waveform travels towards the object, i.e., an organ, and a portion of the waveform is reflected back to the transducer elements in the form of received/reflected ultrasonic energy where the received ultrasonic energy may converted to an electrical energy within the imaging device. The received ultrasonic energy may then be further processed by a number of receive channels to convert the received ultrasonic energy to electrical signals, and the electrical signals may be processed by other circuitry to develop an image of the object for display based on the electrical signals.

An embodiment of an ultrasound imaging device includes a transducer array, and control circuitry including, for example, an application-specific integrated circuit (ASIC), and transmit and receive beamforming circuitry, and optionally additional control electronics.

An imaging device incorporating features of the embodiments may advantageously reduce or resolve issues.

In an embodiment, an imaging device may include a handheld casing where transducers and associated electronic circuitries, such as a control circuitry and optionally a computing device are housed. The imaging device may also contain a battery to power the electronic circuitries.

Thus, some embodiments pertain to a portable imaging device utilizing either pMUT elements or cMUT elements in a 2D array. In some embodiments, such an array of transducer elements is coupled to an application specific integrated circuit (ASIC) of the imaging device.

In the following description, for purposes of explanation, specific details are set forth in order to provide an understanding of the disclosure. It will be apparent, however, to one skilled in the art that the disclosure may be practiced without these details. Furthermore, one skilled in the art will recognize that examples of the present disclosure, described below, may be implemented in a variety of ways, such as a process, one or more processors (processing circuitry) of a control circuitry, one or more processors (or processing circuitry) of a computing device, a system, a device, or a method on a tangible computer-readable medium.

One skilled in the art shall recognize: (1) that certain fabrication operations may optionally be performed; (2) that operations may not be limited to the specific order set forth herein; and (3) that certain operations may be performed in different orders, including being done contemporaneously.

Elements/components shown in diagrams are illustrative of exemplary embodiments and are meant to avoid obscuring the disclosure. Reference in the specification to "one example," "preferred example," "an example," "examples," "an embodiment," "some embodiments," or "embodiments" means that a particular feature, structure, characteristic, or function described in connection with the example is included in at least one example of the disclosure and may be in more than one example. The appearances of the phrases "in one example," "in an example," "in examples," "in an embodiment," "in some embodiments," or "in embodiments" in various places in the specification are not necessarily all referring to the same example or examples. The terms "include," "including," "comprise," and "comprising" shall be understood to be open terms and any lists that follow are examples and not meant to be limited to the listed items. Any headings used herein are for organizational purposes only and shall not be used to limit the scope of the description or the claims. Furthermore, the use of certain terms in various places in the specification is for illustration and should not be construed as limiting.

Turning now to the figures, FIG. 1 is a block diagram of an imaging device 100 with a controller or control circuitry 106 controlling selectively alterable channels (108, 110) and having imaging computations performed on a computing device 112 according to principles described herein. As described above, the imaging device 100 may be used to generate an image of internal tissue, bones, blood flow, or organs of human or animal bodies. Accordingly, the imaging device 100 may transmit a signal into the body and receive a reflected signal from the body part being imaged. Such imaging devices may include either pMUT or cMUT, which may be referred to as transducers or imagers, which may be based on photo-acoustic or ultrasonic effects. The imaging device 100 may be used to image other objects as well. For example, the imaging device may be used in medical imaging; flow measurements in pipes, speaker, and microphone arrays; lithotripsy; localized tissue heating for therapeutic; and highly intensive focused ultrasound (HIFU) surgery.

In addition to use with human patients, the imaging device 100 may be used to acquire an image of internal organs of an animal as well. Moreover, in addition to imaging internal organs, the imaging device 100 may also be used to determine direction and velocity of blood flow in arteries and veins as in Doppler mode imaging and may also be used to measure tissue stiffness.

The imaging device 100 may be used to perform different types of imaging. For example, the imaging device 100 may be used to perform one-dimensional imaging, also known as A-Scan, two-dimensional imaging, also known as B scan, three-dimensional imaging, also known as C scan, and Doppler imaging (that is, the use of Doppler ultrasound to determine movement, such as fluid flow within a vessel). The imaging device 100 may be switched to different imaging modes, including without limitation linear mode and sector mode, and electronically configured under program control.

To facilitate such imaging, the imaging device 100 includes one or more ultrasound transducers 102, each transducer 102 including an array of ultrasound transducer elements 104. Each ultrasound transducer element 104 may be embodied as any suitable transducer element, such as a pMUT or cMUT element. The transducer elements 104 operate to 1) generate the ultrasonic pressure waves that are to pass through the body or other mass and 2) receive reflected waves (received ultrasonic energy) off the object within the body, or other mass, to be imaged. In some examples, the imaging device 100 may be configured to simultaneously transmit and receive ultrasonic waveforms or ultrasonic pressure waves (pressure waves in short). For example, control circuitry 106 may be configured to control certain transducer elements 104 to send pressure waves toward the target object being imaged while other transducer elements 104, at the same time, receive the pressure waves/ultrasonic energy reflected from the target object, and generate electrical charges based on the same in response to the received waves/received ultrasonic energy/received energy.

In some examples, each transducer element 104 may be configured to transmit or receive signals at a certain frequency and bandwidth associated with a center frequency, as well as, optionally, at additional center frequencies and bandwidths. Such multi-frequency transducer elements 104 may be referred to as multi-modal elements 104 and can expand the bandwidth of the imaging device 100. The transducer element 104 may be able to emit or receive signals at any suitable center frequency, such as about 0.1 to about 100 megahertz. The transducer element 104 may be configured to emit or receive signals at one or more center frequencies in the range from about 3.5 to about 5 megahertz.

To generate the pressure waves, the imaging device 100 may include a number of transmit (Tx) channels 108 and a number of receive (Rx) channels 110. The transmit channels 108 may include a number of components that drive the transducer 102, i.e., the array of transducer elements 104, with a voltage pulse at a frequency that they are responsive to. This causes an ultrasonic waveform to be emitted from the transducer elements 104 towards an object to be imaged.

According to some embodiments, an ultrasonic waveform may include one or more ultrasonic pressure waves transmitted from one or more corresponding transducer elements of the imaging device substantially simultaneously.

The ultrasonic waveform travels towards the object to be imaged and a portion of the waveform is reflected back to the transducer 102, which converts it to an electrical energy through a piezoelectric effect. The receive channels 110 collect electrical energy thus obtained, and process it, and send it for example to the computing device 112, which develops or generates an image that may be displayed.

In some examples, while the number of transmit channels 108 and receive channels 110 in the imaging device 100 may remain constant, and the number of transducer elements 104 that they are coupled to may vary. A coupling of the transmit and receive channels to the transducer elements may be, in one embodiment, controlled by control circuitry 106. In some examples, for example as shown in FIG. 1, the control circuitry may include the transmit channels 108 and in the receive channels 110. For example, the transducer elements 104 of a transducer 102 may be formed into a two-dimensional spatial array with N columns and M rows. In a specific example, the two-dimensional array of transducer elements 104 may have 128 columns and 32 rows. In this example, the imaging device 100 may have up to 128 transmit channels 108 and up to 128 receive channels 110. In this example, each transmit channel 108 and receive channel 110 may be coupled to multiple or single pixels 104. For example, depending on the imaging mode (for example, whether a linear mode where a number of transducers transmit ultrasound waves in a same spatial direction, or a sector mode, where a number of transducers transmit ultrasound waves in different spatial directions), each column of transducer elements 104 may be coupled to a single transmit channel 108 and a single receive channel (110). In this example, the transmit channel 108 and receive channel 110 may receive composite signals, which composite signals combine signals received at each transducer element 104 within the respective column. In another example, i.e., during a different imaging mode, each transducer element 104 may be coupled to its dedicated transmit channel 108 and its dedicated receive channel 110. In some embodiments, a transducer element 104 may be coupled to both a transmit channel 108 and a receive channel 110. For example, a transducer element 104 may be adapted to create and transmit an ultrasound pulse and then detect the echo of that pulse in the form of converting the reflected ultrasonic energy into electrical energy.

The control circuitry 106 may be embodied as any circuit or circuits configured to perform the functions described herein. For example, the control circuitry 106 may be embodied as or otherwise include an application specific integrated circuit (ASIC), a field programmable gate array (FPGA), a system-on-a-chip, a processor and memory, a voltage source, a current source, one or more amplifiers, one or more digital-to-analog converters, one or more analog-to-digital converters, etc.

The illustrative computing device 112 may be embodied as any suitable computing device including any suitable components, such as a processor, memory, communication circuitry, battery, display, etc. In one embodiment, the computing device 112 may be integrated with the control circuitry 106, transducers 102, etc., into a single package or single chip, or a single system on a chip (SoC), as suggested for example in the embodiment of FIG. 1. In other embodiments, some or all of the computing devices may be in a separate package from the control circuitry, and the transducers, etc., as suggested for example in the embodiment of in FIG. 2 as will be described in further detail below.

Each transducer element may have any suitable shape such as, square, rectangle, ellipse, or circle. The transducer elements may be arranged in a two dimensional array arranged in orthogonal directions, such as in N columns and M rows as noted herein, or may be arranged in an asymmetric (or staggered) rectilinear array.

Transducer elements 104 may have associated transmit driver circuits of associated transmit channels, and low noise amplifiers of associated receive channels. Thus, a transmit channel may include transmit drivers, and a receive channel may include one or more low noise amplifiers. For example, although not explicitly shown, the transmit and receive channels may each include multiplexing and address control circuitry to enable specific transducer elements and sets of transducer elements to be activated, deactivated or put in low power mode. It is understood that transducers may be arranged in patterns other than orthogonal rows and columns, such as in a circular fashion, or in other patterns based on the ranges of ultrasonic waveforms to be generated therefrom.

Figure 2:
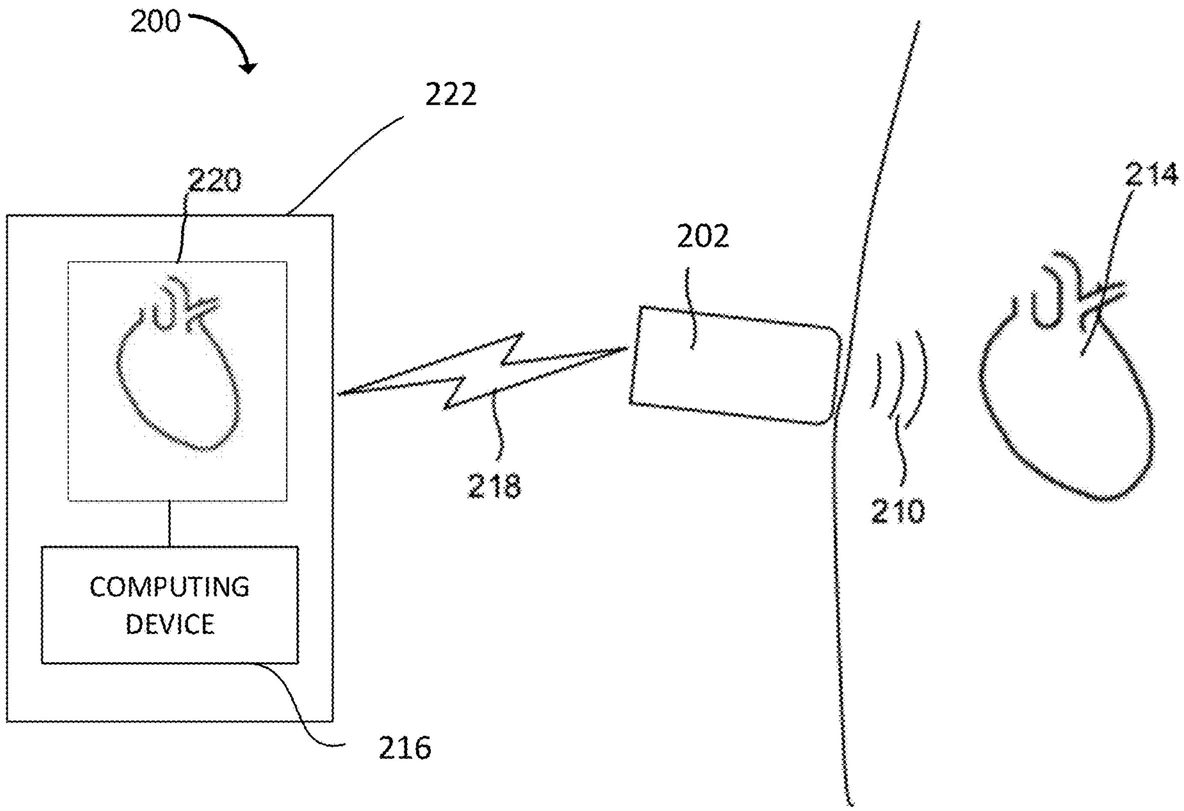
FIG. 2 is a diagram of an imaging system with selectively alterable characteristics, in accordance with disclosed embodiments.

FIG. 2 is a diagram of an imaging environment including an imaging system with selectively configurable characteristics, according to an embodiment. The imaging system of FIG. 2 may include an imaging device 202 and a computing system 222 which includes a computing device 216 and a display 220 coupled to the computing device, as will be described in further detail below.

As depicted in FIG. 2, the computing device 216 may, according to one embodiment, and unlike the embodiment of FIG. 1, be physically separate from the imaging device 220. For example, the computing device 216 and display device 220 may be disposed within a separate device (in this context, the shown computing system 222, physically separate from imaging device 202 during operation) as compared with the components of the imaging device 202. The computing system 222 may include a mobile device, such as cell phone or tablet, or a stationary computing device, which can display images to a user. In another example, as shown in FIG. 1 for example, the display device, the computing device, and associated display, may be part of the imaging device 202 (now shown). That is, the imaging device 100, computing device 216, and display device 220 may be disposed within a single housing.

A "computing device" as referred to herein may, in some embodiments, be configured to generate signals to at least one of cause an image of the object to be displayed on a display, or cause information regarding the image to be communicated to a user. Causing the information regarding the image to be displayed may include causing identifying information regarding an identified vessel, and recommendations regarding a foreign object such as a catheter to be inserted into the vessel, to be communicated to a user via a user interface, such as by being displayed on a display, via a voice message to be played through a speaker, and/or text on the UI display. The generation of the signals may include, in some embodiments, implementing a vessel detection and tracking algorithm as will be described further below.

As depicted, the imaging system includes the imaging device 202 that is configured to generate and transmit, via the transmit channels (FIG. 1, 108), pressure waves 210 toward an object, such as a heart 214, in a transmit mode/process. The internal organ, or other object to be imaged, may reflect a portion of the pressure waves 210 toward the imaging device 202 which may receive, via a transducer (such as transducer 102 of FIG. 1), receive channels (FIG. 1, 110), control circuitry (FIG. 1, 106), the reflected pressure waves. The transducer may generate an electrical signal based on the received ultrasonic energy in a receive mode/process. A transmit mode or receive mode may be applicable in the context of imaging devices that may be configured to either transmit or receive, but at different times. However, as noted previously, some imaging devices according to embodiments may be adapted to be in both a transmit mode and a receive mode simultaneously. The system also includes a computing device 216 that is to communicate with the imaging device 100 through a communication channel, such as a wireless communication channel 218 as shown, although embodiments also encompass within their scope wired communication between a computing system and imaging device. The imaging device 100 may communicate signals to the computing device 216 which may have one or more processors to process the received signals to complete formation of an image of the object. A display device 220 of the computing system 222 may then display images of the object using the signals from the computing device. The computing system may further convey information to a user regarding a defective pixel as noted above.

An imaging device according to some embodiments may include a portable device, and/or a handheld device that is adapted to communicate signals through a communication channel, either wirelessly (using a wireless communication protocol, such as an IEEE 802.11 or Wi-Fi protocol, a Bluetooth protocol, including Bluetooth Low Energy, a mmWave communication protocol, or any other wireless communication protocol as would be within the knowledge of a skilled person) or via a wired connection such as a cable (such as USB 2, USB 3, USB 3.1, and USB-C) or such as interconnects on a microelectronic device, with the computing device. In the case of a tethered or wired, connection, the imaging device may include a port as will be described in further detail in the context of FIG. 3 for receiving a cable connection of a cable that is to communicate with the computing device. In the case of a wireless connection, the imaging device 100 may include a wireless transceiver to communicate with the computing device 216.

It should be appreciated that, in various embodiments, different aspects of the disclosure may be performed in different components. For example, in one embodiment, the imaging device may include circuitry (such as the channels) to cause ultrasound waveforms to be sent and received through its transducers, while the computing device may be adapted to control such circuitry to the generate ultrasound waveforms at the transducer elements of the imaging device using voltage signals, and further a processing of the received ultrasonic energy to determine a defective pixel dataset for one or more defective pixels. In such an embodiment, the computing device may manage/control a functioning of the imaging device based on the determination of the defective pixels, may construct images of the object using frames as discussed in more detail below, may select and configure transmit and receive channels, etc.

In another embodiment, the imaging device may include control circuitry to control a generation of the ultrasound waveforms at the transducer elements using voltage signals in order to cause the ultrasound waveform to be sent and received from the transducer elements, and may also generate electrical signals from the received ultrasound energy, and, in a test mode, use electrical signals corresponding to the received ultrasound waveforms to determine information regarding one or more defective pixels of the imaging device. In such an embodiment, the control circuitry of the imaging device may send the electrical signals generated from the received ultrasound energy to the computing device, which may process them in order to determine the information regarding one or more defective pixels. More generally, it should be appreciated that any suitable function disclosed herein may be performed by one or more circuitries, and that these circuitries may be housed in one physical device, or housed physically separately from each other, but communicatively coupled to one another.

Figure 3:
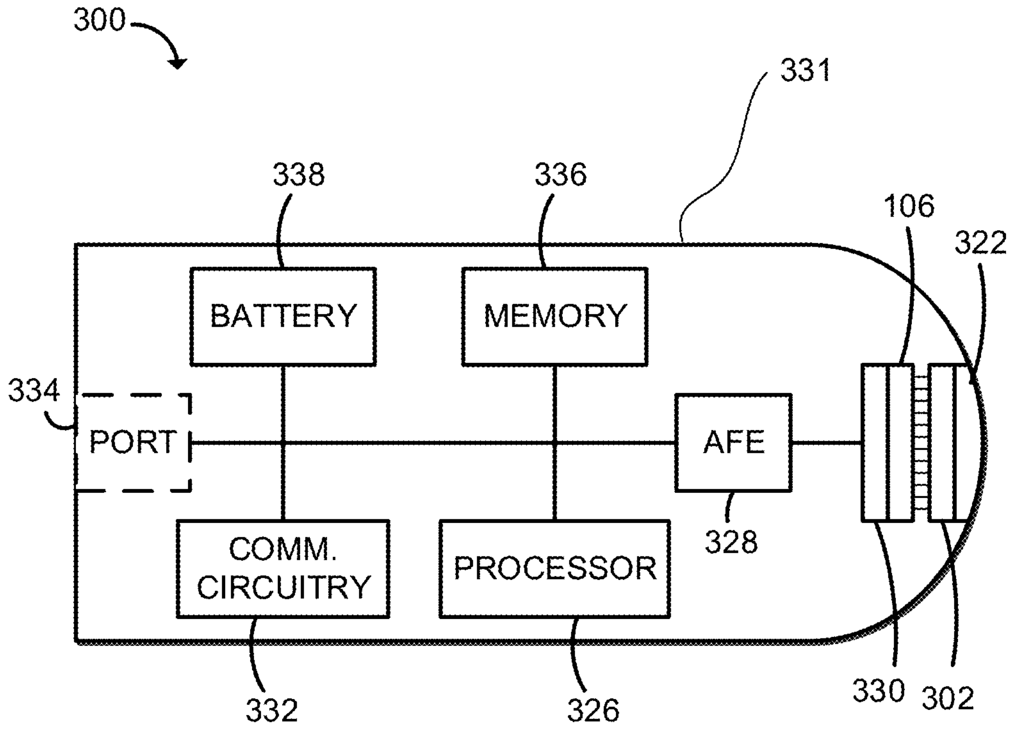
FIG. 3 is a schematic diagram of an imaging device with selectively alterable characteristics, in accordance with disclosed embodiments.

FIG. 3 represents a view of an imaging device according to some embodiments, as will be described in further detail below.

As seen in FIG. 3, the imaging device 300 may include a handheld casing 331 where transducers 302 and associated electronics are housed. The imaging device may also contain a battery 338 to power the electronics. FIG. 3 thus shows an embodiment of a portable imaging device capable of 2D and 3D imaging using pMUTs in a 2D array, optionally built on a silicon wafer. Such an array coupled to an application specific integrated circuit (ASIC) 106 with electronic configuration of certain parameters, enables a higher quality of image processing at a low cost than has been previously possible. Further by controlling certain parameters, for example the number of channels used, power consumption may be altered and temperature may be changed.

The imaging device 300 according to some embodiments is configured to allow system configurability and adaptability in real time based on information regarding one or more defective pixels (defective pixel data). This is done for example by comparing a current pixel performance dataset of one or more pixels of a transducer array of an imaging device with a baseline pixel performance dataset of the same pixels as will be explained in further detail below.

Now addressing FIG. 3 in more detail, FIG. 3 is a schematic diagram of an imaging device 300 with selectively adjustable features, according to some embodiments. The imaging device 300 may be similar to imaging device 100 of FIG. 1, or to imaging device 202 of FIG. 2, by way of example only. As described above, the imaging device may include an ultrasonic medical probe. FIG. 3 depicts transducer(s) 302 of the imaging device 300. As described above, the transducer(s) 302 may include arrays of transducer elements (FIG. 1, 104) that are adapted to transmit and receive pressure waves (FIG. 2, 210). In some examples, the imaging device 300 may include a coating layer 322 that serves as an impedance matching interface between the transducers 302 and the human body, or other mass or tissue through which the pressure waves (FIG. 2, 210) are transmitted. In some cases, the coating layer 322 may serve as a lens when designed with the curvature consistent with focal length desired.

The imaging device 300 may be embodied in any suitable form factor. In some embodiments, part of the imaging device 300 that includes the transducers 302 may extend outward from the rest of the imaging device 100. The imaging device 300 may be embodied as any suitable ultrasonic medical probe, such as a convex array probe, a micro-convex array probe, a linear array probe, an endovaginal probe, endorectal probe, a surgical probe, an intraoperative probe, etc.

In some embodiments, the user may apply gel on the skin of a living body before a direct contact with the coating layer 322 so that the impedance matching at the interface between the coating layer 322 and the human body may be improved. Impedance matching reduces the loss of the pressure waves (FIG. 2, 210) at the interface and the loss of the reflected wave travelling toward the imaging device 300 at the interface.

In some examples, the coating layer 322 may be a flat layer to maximize transmission of acoustic signals from the transducer(s) 102 to the body and vice versa. The thickness of the coating layer 322 may be a quarter wavelength of the pressure wave (FIG. 2, 210) to be generated at the transducer(s) 102.

The imaging device 300 also includes a control circuitry 106, such as one or more processors, optionally in the form of an application-specific integrated circuit (ASIC chip or ASIC), for controlling the transducers 102. The control circuitry 106 may be coupled to the transducers 102, such as by way of bumps. As described above, the transmit channels 108 and receive channels 110 may be selectively alterable or adjustable, meaning that the quantity of transmit channels 108 and receive channels 110 that are active at a given time may be altered such that, for example, one or more pixels determined to be defective are not used. For example, the control circuitry 106 may be adapted to selectively adjust the transmit channels 108 and receive channel 110 based on pixels to be tested for defects, and/or based on pixels determined to be defective.

In some examples, the basis for altering the channels may be a mode of operation, the mode of operation may in turn be chosen based on which pixels are determined to be defective, and optionally based on the type of defect of each defective pixel.

The imaging device may also include one or more processors 326 for controlling the components of the imaging device 100. One or more processors 326 may be configured to, in addition to control circuitry 106, at least one of control an activation of transducer elements, process electrical signals based on reflected ultrasonic waveforms from the transducer elements or generate signals to cause generation of an image of an object being imaged by one or more processors of a computing device, such as computing device 112 of FIG. 1 or 216 of FIG. 2. One or more processors 326 may further be adapted to perform other processing functions associated with the imaging device. The one or more processors 326 may be embodied as any type of processors 326. For example, the one or more processors 326 may be embodied as a single or multi-core processor(s), a single or multi-socket processor, a digital signal processor, a graphics processor, a neural network compute engine, an image processor, a microcontroller, a field programmable gate array (FPGA), or other processor or processing/controlling circuit. The imaging device 100 may also include circuit(s) 328, such as Analog Front End (AFE), for processing/conditioning signals, and an acoustic absorber layer 330 for absorbing waves that are generated by the transducers 102 and propagated towards the circuits 328. That is, the transducer(s) 102 may be mounted on a substrate and may be attached to an acoustic absorber layer 330. This layer absorbs any ultrasonic signals that are emitted in the reverse direction (i.e., in a direction away from coating layer 322 in a direction toward port 334), which may otherwise be reflected and interfere with the quality of the image. While FIG. 3 depicts the acoustic absorber layer 330, this component may be omitted in cases where other components prevent a material transmission of ultrasound in the reverse direction.

The analog front end 328 may be embodied as any circuit or circuits configured to interface with the control circuitry 106 and other components of the imaging device, such as the processor 326. For example, the analog front end 328 may include, e.g., one or more digital-to-analog converters, one or more analog-to-digital converters, one or more amplifiers, etc.

The imaging device may include a communication unit 332 for communicating data, including control signals, with an external device, such as the computing device (FIG. 2, 216), through for example a port 334 or a wireless transceiver. The imaging device 100 may include memory 336 for storing data. The memory 336 may be embodied as any type of volatile or non-volatile memory or data storage capable of performing the functions described herein. In operation, the memory 336 may store various data and software used during operation of the imaging device 100 such as operating systems, applications, programs, libraries, and drivers.

In some examples, the imaging device 100 may include a battery 338 for providing electrical power to the components of the imaging device 100. The battery 338 may also include battery charging circuits which may be wireless or wired charging circuits (not shown). The imaging device may include a gauge that indicates a battery charge consumed and is used to configure the imaging device to optimize power management for improved battery life. Additionally or alternatively, in some embodiments, the imaging device may be powered by an external power source, such as by plugging the imaging device into a wall outlet.

Some embodiments overcome disadvantages over the prior art with respect to identification of vessels in a body, such as a vessel within which fluid flows, such as a vessel of a living body within which fluid flows, that would mitigate issues with vessel detection for the insertion of foreign bodies into the vessel, especially where fluid may flow within the vessel. Computer algorithms according to some embodiments enable the detection and tracking of vessels within which a fluid flows (hereinafter "vessels") this way facilitating the detection of blood vessels for medical intervention, such as the insertion of a foreign body (e.g. a needle or catheter or the like).

According to some embodiments, the algorithm may relies not only on A, B or C-mode imaging by an ultrasonic device for vessel detection, but also on imaging the allows the determination of fluid flow within a detected vessel.

Typically, by way of example in B-mode (2 dimensional) ultrasonic images, veins and arteries appear as dark, oval regions on the displayed image when seen in a short-axis view (i.e., in a cross sectional view taken perpendicular to the direction of blood flow). In principle, according to some embodiments, a computer algorithm including object recognition may be implemented to detect or identify vessels in an A, B or C-mode ultrasound image sequence by detecting a presence of such oval regions.

By itself, an object detector yields inadequate vessel detection performance due to the presence of confounding tissue texture and imaging artifacts in the displayed image or image frame. Furthermore, when veins are collapsed by the force of the imaging probe during the procedure, they may become impossible to detect in an individual B-mode image frame.

A novel aspect of embodiments is the use of additional flow information, beyond what is seen in an individual image ultrasonic frame, such as a B-mode frame. The use of such additional flow information can enhance the accuracy and computational efficiency of vessel detection and identification. Some embodiments use two additional sources of information beyond a single ultrasonic image frame (such as a B-mode image frame): 1) flow data (such as Doppler flow data, including either color Doppler or power Doppler), and 2) one or more ultrasonic image frames preceding the current ultrasonic image frame (such as a B-mode image frame) in the time domain. In some embodiments, flow data refers to flow data only for flow that has a component perpendicular to a plane of the ultrasonic images used to detect and track a vessel.

In the context of the instant description, when referring to an "ultrasonic image" or "ultrasonic images" in the singular or in the plural, what is being referred to is one or more images generated as a result of using an ultrasonic device. The one or more images could include A-mode, B-mode or C-mode images, and preferably B-mode (two dimensional images).

In some instances, less-experienced ultrasound human users may find flow images, such as flow images obtained using Doppler imaging, confusing, since such images may sometimes be noisy, and may be displayed overlaid on the ultrasonic image, thereby obscuring the anatomical detail depicted within the ultrasonic image. A feature of some embodiments is that information or data acquired through flow imaging may be acquired and used by the computer algorithm "behind the scenes," that is, it may not be displayed to a human user, but consumed by the computer algorithm in order to identify a vessel in a body. Thus, according to one example, Doppler imaging data may be processed by an algorithm according to some embodiments to promote more accurate and more efficient vessel detection by a computing device.

Some embodiments recognize that object recognition through ultrasound may benefit from identifying image locations worthy of being searched further in order to recognize/detect/identify the object. Usually these locations are identified from the image itself. However, some embodiments use a separate flow image (such as either color Doppler or power Doppler) to identify candidate locations for finding vessels in the corresponding ultrasonic image (these locations are referred to herein as flow seeds), or as confirmatory information regarding whether an object identified as a vessel in which fluid flows is indeed a vessel in which fluid flows. Doppler information may be effective in this task, because flow detection is a good signature or indicator of the presence of a vessel.

If a spatial location exhibits flow determined based on flow data (such as data obtained through Doppler imaging), and strong evidence of a predetermined shape (such as an elliptical shape) centered near the same location in the corresponding B-mode image, then this suggests high confidence that a vessel is present at this location-greater confidence than what is provided by either signature (i.e. flow only or ultrasonic image frame only) considered individually. Some embodiments exploit this idea by searching an ultrasonic image for the predetermined shape in proximity to flow seeds, such as Doppler seeds. The type of flow, such as whether pulsating based on heart rate, may indicate an artery, versus a comparatively more constant flow may indicate a vein. The above technique not only improves detection performance of a computing device, but also reduces the search space, yielding valuable computational efficiency. An alternative approach is to use flow information to complement data indicating an ultrasonic image of a vessel from an ultrasonic deep-learning detector when computing confidence of the presence of a vessel.

Some embodiments incorporate predictive tracking as a further source of seed locations to be searched (in addition to the Doppler seeds). These "tracker seeds" are obtained by using the shape, location, and/or apparent translational velocity of each vessel (due to relative motion of the vessel and the probe) detected in the current frame to predict the shape and location of that vessel in the next frame. Tracking improves detection performance by exploiting interframe consistency. If the algorithm suspects that a vessel is present in a given image frame, the fact that it has the expected shape and location enhances confidence in this conclusion.

Tracking also reduces the ranges of shapes and locations of ellipses that must be searched, thereby reducing computational burden.

In alternative embodiment, rather than separate object detection and tracking, a spatio-temporal detection method may be used which jointly analyzes recent image frames to make a vessel detection decision for the current frame. A spatio-temporal detection method involves a two dimensional spatial dimension and a third dimension based on time. This may be done, for example, using a multichannel implementation of the You Only Look Once (YOLO) algorithm (in which the current frame and a set of preceding frames serve as the channels) or the combination of a convolutional neural network (which performs spatial analysis) and long short-term memory network (which performs temporal analysis).

In addition to their accuracy benefits, tracking and spatio-temporal detection allow the algorithm to keep track of which vessel is which (e.g. artery versus vein), permitting consistent annotation on the user interface, and allowing parameters of each vessel to be analyzed temporally for purposes of detection and discrimination of veins and arteries.

In a preferred embodiment, a similar tracking approach to that used for ultrasound imaging may also be applied to a concurrently acquired flow data, such as concurrently applied Doppler flow video. Doppler tracking increases the confidence in the tracker seed locations (analogous to the confidence boost described above in the context of beginning with flow seeds and following up with ultrasonic imaging), and enables each vessel to be uniquely tracked in the Doppler sequence so that the flow information may be analyzed by motion-compensated temporal processing for use in vein-artery discrimination.

In a preferred embodiment, Doppler information may be used to produce evidence as to a vessel's identity as a vein or artery by applying signal processing methods to analyze the periodic behavior of flow as evidence of pulsatility (a feature typically associated with arteries). In some embodiments, a determination as to pulsatility of a vessel may be accomplished by a machine learning classifier. The machine learning classifier may use ultrasonic image data, or it may use measurements of a scalar index of pulsatility. In some embodiments, pulsatility may be determined by a computing device by analyzing data relating to spatial movements in proximity to a vessel as between successive ultrasound images. In alternative embodiments, pulsatility may be assessed by local analysis of anatomical motion (e.g. of the vessel walls) in the ultrasonic imagery.

In the upper arm, where peripherally inserted central catheter (PICC) and central venous catheter (CVC) lines (as examples of foreign objects to be inserted into bodily vessels) are generally placed, there is only one major artery, the brachial artery, which artery is very close to brachial veins. The other two major veins—the basilic vein and the cephalic vein—are further separated from the brachial artery. Thus, in the upper arm, if a large vessel, imaged by the ultrasound device of some embodiments, is not immediately adjacent to any other large vessel, it is more likely a vein than an artery, because the only artery will have other large vessels close to it. An upper arm major vein not close to any other major vessel of the upper arm is one of two preferred bodily veins for line access. Some embodiments may use an flow information, along with ultrasonic images, to detect blood vessel location, and may, in this way, provide a strong signature for vein-artery discrimination, such as in the upper arm. Such signature may be provided by using data on vessel location, pulsatility and/or compressibility, along with flow data. This may be done by using each of these individually or in combination, combined using machine learning or by simple Boolean logic.

Within the context of some embodiments, each vessel may be accessed in real-time (during detection and tracking of a blood vessel), or at the end of the imaging session involving detection and tracking of a blood vessel.

A blood vessel may best be accessed only if it is a vein having certain characteristics. The vein may best be compressible, because incompressibility can imply that the vein contains a clot, which may break off and travel to the lungs if the vessel is accessed. In standard practice, the operator of the probe observes compressibility by using the probe to apply pressure to the tissue, thereby squeezing the vessels. In some embodiments, compressibility is measured automatically. The vein may best have a sufficient diameter to accommodate a catheter, in accordance with vessel occupancy standards that are generally established by a providing healthcare institution. As described previously, arteries may best be avoided. In the upper arm, since the preferred veins (basilic and cephalic) for access by a needle or catheter are not near any artery, an isolated vessel may be detected by an algorithm according to some embodiments to be a vein rather than an artery, and as such safely distant from any artery because it is in the upper arm, and not near any other large vessels.

In summary, for a vessel to be a good candidate to be accessed for catheter placement or needle placement, it may, according to some embodiments meet the following criteria: 1) be a vein, 2) be compressible, and 3) have a diameter should be sufficiently large to accommodate the foreign object to be inserted therein. In the upper arm, there is an additional criterion which may be applied, that the vessel should not be close to other comparably large vessels/may be isolated from other comparably large vessels.

In a preferred embodiment, suitability for vascular access may be determined by a computing device by way of accessing a logical truth table based on the relevant criteria. In alternative embodiments, measures of these criteria may serve as features for use by a machine learning algorithm run on the computing device.

Some embodiments include a system of algorithmic processing components and a user interface component. In a preferred embodiment, these components may operate as described further below.

Some embodiments include a novel user interface (UI) that defines the functionality and manner of information presentation pertaining to detection and tracking of a vessel using ultrasonic imaging.

Some embodiments pertain to algorithms having algorithmic components described in greater detail herein, executed on one or more processors of a computing system, such as computing system 112 or 216, to provide information displayed in the user interface, the information including identification of a vessel, and information regarding its accessibility by one or more foreign objects, such as a catheter and/or a needle.

According to some embodiments, the algorithm is to implement detection and tracking of a vessel, including for example providing an outline of the vessel on the UI. According to embodiments related to detection and track, a potential vessel may be detected by the Vessel Scouting Function (VSF) of an algorithm. Once a potential vessel, or a candidate vessel, is detected for access, the algorithm may continuously determine and cause displaying an outline of its boundary and the location of its center or a its diameter, and may also predicts its outline, apparent velocity (due to relative motion of the tissue and probe), and location of the vessel in a next frame, for purposes of vessel tracking.

An algorithmic component of an algorithm according to some embodiments may implement a discrimination as between veins and arteries. In this component, the algorithm may continuously seek to perform such discrimination. Discrimination may be implemented by using criteria such as compressibility, pulsatility and spatial location in conjunction with a shape on an ultrasonic image, such as an elliptical shape in a B-mode image.

An algorithmic component of an algorithm according to some embodiments may automatically determine parameters or attributes of a vessel, such as its compressibility, its pulsatility, its diameter, its depth (or distance from the surface of the skin), its suitability for access, the fluid flow (or flow rate) therein, to name a few. A recommendation of foreign object selection for insertion, such as a catheter, may then be displayed to the user on the UI.

Figure 4:
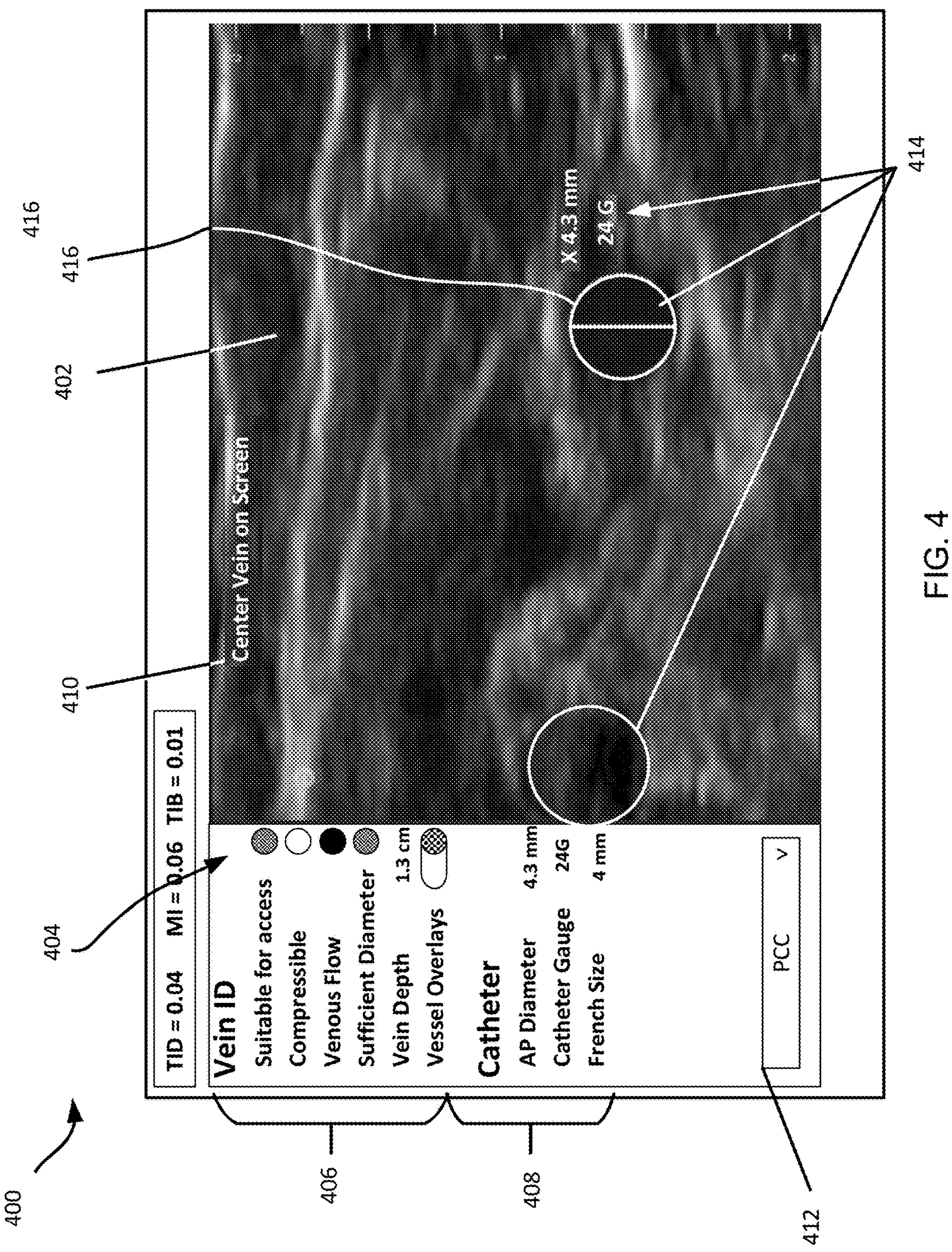
FIG. 4 depicts an embodiment of a touchscreen user interface (UI) according to Some embodiments, which displays a real-time B-mode ultrasound image sequence, along with various interpretive overlays, virtual indicator lights, measurements, recommendations, controls and parameters.

FIG. 4 depicts an embodiment of a touchscreen user interface (UI) 400 according to some embodiments. The display of UI 400 displays a real-time B-mode ultrasound image sequence 402, along with various interpretive overlays, virtual indicator lights 404, vessel parameters 406, noting that a vessel parameter (or vessel attribute) as used herein may include any of one or more vessel dimensions (such as diameter/radius, and depth), vessel fluid flow rate, vessel pulsatility, vessel compressibility, or vessel outline on an ultrasonic image. A vessel parameter may further include vessel suitability for access based on the foreign object to be inserted therein. The UI may include text communication to the user 410, and may further include a feature 412 to allow selection, by the user, of the type of foreign object to be inserted, in the shown case a catheter that is a PCC.

According to some embodiments, as shown by way of example in FIG. 4, a series of B mode images may be displayed in real-time as time progresses. Veins and arteries may be caused to be shaded on the display by the algorithm using a color code (for example, red for artery, blue for vein). A specific candidate vessel for catheter placement may be outlined. Other styles of annotation, such as crosshairs, can substitute for outlines and shading. The algorithm may select a vein as the candidate vessel and indicate its attributes in an overlay 414 and in the "Vein ID" section 406 of the interface. A "Vessel Overlays" toggle switch may be provided to allow the user to turn off the overlays. If the user is interested in seeing the attributes of a different vessel, some algorithms may provide an option to touch on a different vessel, and the algorithm may then outline that different vessel as the candidate vessel and provide the new vessel's attributes. Next to the candidate vein 416 is shown its anterior-posterior (AP) diameter (reported, for example, in millimeters), as well as the recommended catheter associated with that diameter (chosen based on guidelines set by the healthcare institution). The vertical line segment "caliper" within the outlined candidate vein 416 depicts the path along which the AP diameter is measured. This path may be computed automatically by the algorithm.

An algorithm according to some embodiments may report automated (i.e. determined by the algorithm) findings about an outlined vessel on the UI, for example in the form of vein ID 406 in FIG. 4. "Vein depth" is a numeric value measured automatically as the distance (e.g. in cm) from the skin line (top of image) to the uppermost point on the vein outline. "Vein ID" may include four colored (shown by way of patterns (no pattern, textured pattern, and solid pattern) in FIG. 4), virtual indicator lights conveying automatically-determined information about the candidate vessel outlined on the image display.

"Compressible" (green or red) indicates whether the candidate vessel may be collapsed by applying pressure to the tissue using the ultrasound probe (veins are typically compressible, while arteries are usually not). "Venous flow" (green or red) indicates whether or not the vessel is exhibiting a blood flow pattern that is indicative of a vein (flow is typically more pulsatile in an artery than in a vein; this pulsatility may be measured using Doppler flow information and or pulsating motions of the vessel seen in the B-mode images). "Sufficient diameter" (green, yellow or red) indicates whether the AP diameter is large enough to be targeted for catheter placement based on guidelines set by the healthcare institution. A yellow indication denotes that the diameter is borderline. "Suitable for access" (green, yellow or red) indicates whether the vein meets the criteria for catheter placement. The "Catheter selection" section repeats the AP diameter, and shows the corresponding recommended catheter gauge and French size, obtained based on permitted percent occupancy of the vessel by the catheter, as determined by the healthcare institution.

Other graphical elements in FIG. 4 may a user profile button, and ultrasound imaging parameters.

Figure 5:
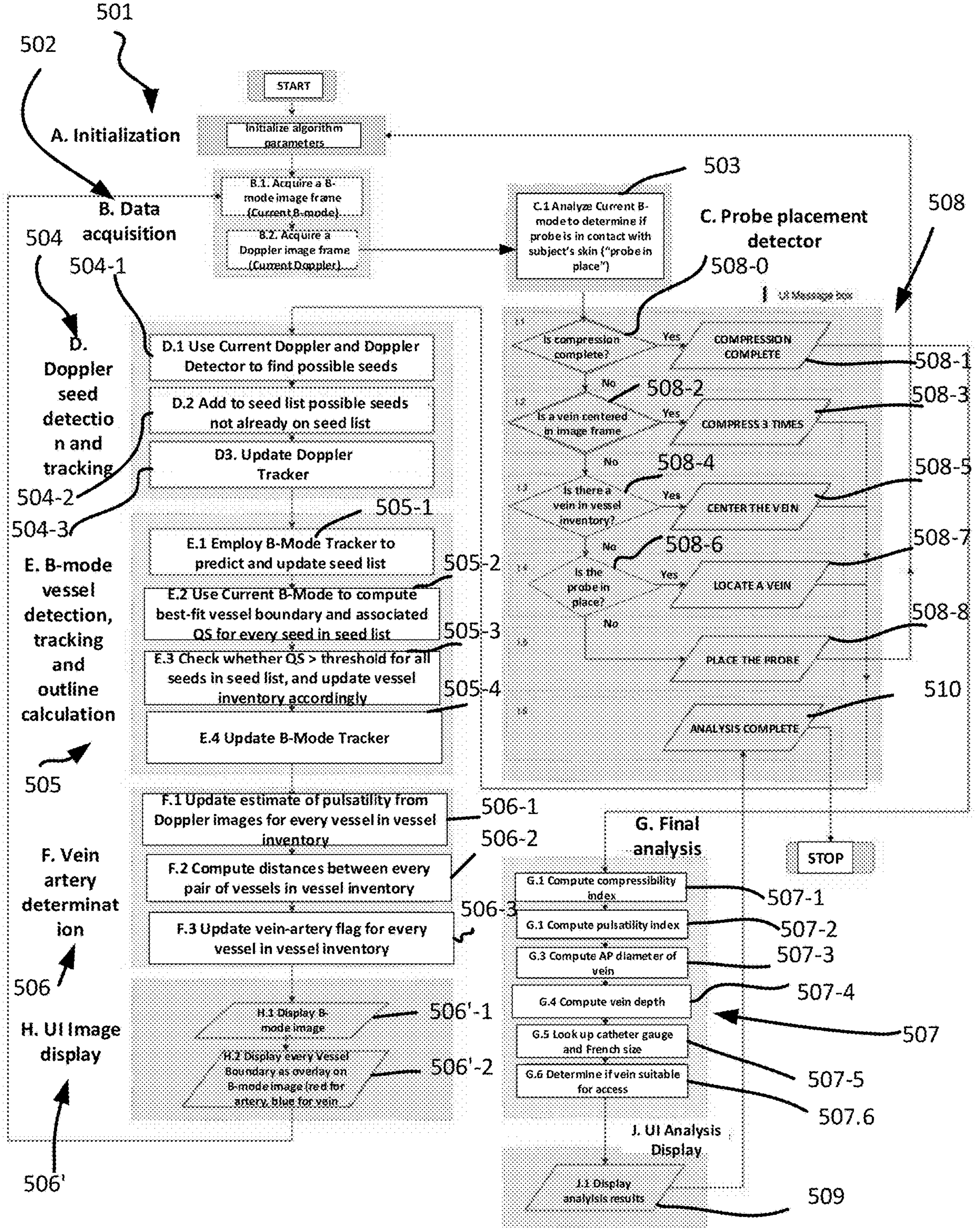
FIG. 5 depicts, in flowchart form, the operations of the blood vessel detection, outlining, tracing and characterization algorithm, as implemented in an ultrasound imaging system, according to one embodiment.

FIG. 5 depicts, in flowchart form, an exemplary process for blood vessel detection, outlining, tracing and characterization algorithm, as implemented in an ultrasound imaging system, according to one embodiment. Functional blocks or stages implemented or executed by the algorithm 500 are cross-referenced in the flowchart in FIG. 5.

Operation 501 performs initialization, including without limitation, one or more of the following algorithm parameters:

- search parameters: initial ranges of parameter values to be considered when searching for a best-fit vessel candidate:
  - starting from a B-mode image, for example, determining parameters to search for and identify one or more substantially elliptical (including circular) shapes each within a range of predetermined parameter values; for example, aspect ratio between 0 and 1; long-axis radius between 1 mm and 3 mm; orientation angle between 0 and 45 degrees; and no limit on the vessel's location within the image.
  - starting from flow information, determining parameters for detecting flow seeds or Doppler seeds using Doppler or a Doppler tracker; for example, the flow seed locations may be obtained as the local maxima of measured flow.
- vessel inventory: using a data structure containing, for each vessel currently being tracked by the algorithm: an identifier code, a center location, shape parameters, and apparent velocity (translational displacement per frame);
- seed list: data structure containing list of spatial image locations (found as described above) that are candidates to search for a predetermined vessel shape, such as an ellipse.

At operation 502, an exemplary algorithm may perform data acquisition, including without limitation the following:

- at operation 502-1: acquiring a B-mode image frame (Current B-mode). In this Operation, a B-mode image frame may be acquired in a standard way.
- At operation 502-2: acquiring a Doppler flow (color doppler or power Doppler) image frame (Current Doppler). In the operation 502-2, a Doppler image frame is acquired in the standard way. In a preferred embodiment, Current Doppler covers the same field of view as Current B-mode. In alternative embodiments, the Current Doppler includes only a subset of the image information, for example:
  - full field of view initially, then switching to partial fields of view until such time that the probe is not in contact with the skin (which is equivalent to beginning from scratch);
  - set of all pixels within a pre-specified number of pixels of the left, right and/or bottom edge of Current B-mode, so as to seek vessels that were not within the B-mode field of view in the previous frame, but are present in the current field of view due to motion of the probe. It is to be noted that a vessel cannot enter the field of view through top edge of the image, where the skin line resides. As a result, according to some embodiments, an algorithm may apply Doppler imaging to only image regions near these edges to detect the appearance of vessels not yet seen;
  - subsets of the full field of view, such as small regions of interest or individual scan lines, which the algorithm may request to be acquired by the probe. Such requests may be useful, for example, in the following situation. Suppose the B-mode Tracker has been following a given vessel in a series of image frames through time, and predicts it to be present in the next image frame with given location and shape parameters. Now suppose that upon searching based on these parameters, the Quality Score (described below) does not lead to detection of a vessel as anticipated. In this case, the algorithm may request the probe to interrogate, using Doppler flow imaging, a small image region surrounding the predicted location so as to determine whether the small image region is still a good candidate for vessel search. If so, then the B-mode Tracker may be re-seeded.

The algorithm at operation 503 detects placement of the ultrasonic probe. An ultrasound scan begins when the ultrasound probe is placed in contact with the skin (which may coated in ultrasound gel). Therefore, the algorithms are by-passed (dormant) until the probe is in place. If the probe is lifted from the skin during a scan, the algorithms are again by-passed and the algorithm parameters are re-initialized. The condition "probe in place" may be detected by measuring the average image intensity of the pixels within X % of the bottom of the image, and comparing this value to a threshold determined T. The percentage X and threshold T may be determined based on example scans at various depth and gain settings for the specific ultrasound probe.

An exemplary algorithm at operations 504 and 505 performs Doppler seed detection and tracking and B-mode vessel detection, tracking and outline calculation. The algorithm 500 contains two detector/tracker pairs: one for Doppler; one for B-mode.

The Doppler Detector 504-1 searches the Doppler image frame for possible flow seeds. Its search is guided by the Doppler Tracker 504-2, which focuses this search based on the last known location of possible flow seeds. The Doppler Tracker 504-2 also keeps track of the seeds (track of which current seed corresponds to which prior seed). The B-mode Detector 505 uses the possible seeds identified by the Doppler Detector/Tracker as a starting point for searching the B-mode image for vessels.

The B-mode Detector 505's search for vessels may be guided by a set of search parameters provided by the B-mode Tracker. In summary, the two detector/tracker pairs work together in the following way: the Doppler Detector/Tracker 504 keeps track of flow seeds, while the B-mode Detector/Tracker 505 uses that information to look for and keep track of the vessels. The process may start with identifying a B-mode seed first, and basing Doppler detection on the region of the B-mode seed, or by identifying a Doppler seed first, and basing B-mode detection on the region of the Doppler seed.

An exemplary algorithm may use a Doppler Detector to perform operation 504-1. For operation 504-1, to begin, the search window to find possible seeds is the entire image. In this block, possible seeds may be identified from the Current Doppler as follows:

(1) based on Current Doppler, create a component image f1 (or at least data f1) that contains flow information only for pixels exhibiting one of the two possible flow directions (toward the probe or away from the probe);

(2) generate a binary signal map f2 from f1 by comparing f1 against a threshold TO (to remove weak or noisy signal values), and eliminate regions in f1 that are too small in spatial extent (suggesting that they depict noise or small vessels that are not of interest);

(3) declare no detection at the UI if the total signal area in f2 exceeds a pre-determined threshold (which happens when the probe motion overwhelms the motion due to blood flow) or is smaller than a pre-determined threshold (likely corresponding to noise or small vessels).

(4) locate a signal region R0 in f2;

(5) find an interior point P in R0 (e.g., the centroid of R0), and declare P as a possible flow seed.

An exemplary algorithm at operation 504-1(2) above includes tuning TO for best performance, and is dependent on how Current Doppler is scaled before being input to the algorithm. For example, TO may be chosen to be 0.1 times the maximum value in Current Doppler. Likewise, choice of the threshold values for determining a region to be too large or too small by the algorithm at operations 504-1(2) and (3) is dependent on the spatial resolution of Current Doppler. These threshold values may be set according to the size of the smallest or largest vessels of interest.

At operation 504-2, the algorithm may add possible seeds to the seed list. If any of the possible seeds identified in D.1 are not already in the seed list, then add them to the seed list. In the seed list, the location and maximum flow amplitude ("flow score") for each possible seed may be recorded in a memory of the computing device.

The algorithm may, at operation 504-3, update the Doppler Tracker. The Doppler Tracker may serves two purposes: 1) it may limits the region(s) of the image being searched in 504-1 for Doppler signal based on the locations of the seeds in of the seed list, and 2) it may keep track of which seed is which.

In a preferred embodiment, when the scan begins, the search window for detection of flow may encompass the entire image frame. Thereafter, the Doppler tracker may defines a search window for the detection in 504-1, for each seed in the seed list. The search window for a given seed is a box centered at a point defined by the seed's last known location, plus a predicted motion vector for the current frame. Currently, the box is 16×16 pixels. In other variations, the motion vector may be omitted for one or both directions.

For each frame, the Doppler Tracker may check whether the search for a given seed is going outside the boundaries of the image. If so, the algorithm may determine that tracking of the seed has failed, and it is no longer tracked, and may indicate the same to the user via the UI.

Because Doppler images are noisy, it is possible that a seed becomes undetectable in one or more consecutive frames. To address this issue, if a seed undetectable, the Doppler Tracker continues to track its predicted position for some period of time, such as 0.5 sec. If the seed re-appears, then it continues to be tracked as normal. If not, the tracking of that seed is discontinued.

An example algorithm may perform B-mode vessel detection, tracking and outline calculation at operation 505.

At operation 505-1, an exemplary algorithm may employ a B-mode Tracker to predict and update the seed list. In operation 505-2, the algorithm may use a Current B-mode to compute a best-fit vessel boundary and Quality Score (QS). In operation 505-3, the algorithm is to determine whether an ellipse (vessel) is present. In Operation 505-4, the algorithm is to update the B-mode tracker by updating the vessel parameter values of each seed using the values in found in operation 505-2.

In the preferred embodiment, a vessel is characterized by an ellipse which outlines the vessel boundary. The ellipse may be determined by any well-known method as would be within the knowledge of a skilled person. However, alternative approaches for determining the ellipse could be used instead, as will be obvious to those skilled in the art.

Quality Score is a metric that quantifies the degree to which an ellipse accurately describes the signature of a particular vessel in a B-mode image. In a preferred embodiment, the Quality Score of a vessel may be measured by the strength of image gradient averaged over a set of N points evenly placed at the vessel boundary. The image gradient represents a quantification of the contrast of the vessel boundary in B-mode. The number of points N may set between 20 and 50, with lower values for smaller vessels and higher values for larger vessels.

The Vessel Boundary may be defined as the shape outlining the vessel in B-mode (e.g. ellipse) that produces the largest or maximum Quality Score when computed by the computing device at a given image location, with determination of a location for the maximum Quality Score performed by the computing device using a grid search over the shape parameters by the algorithm at operation 505-2. For example, for an ellipse model of the vessel shape, the grid search may be based on the parameters of an ellipse: center location coordinates, long-axis radius, aspect ratio and orientation angle.

In operation 505-3, the algorithm may determine a vessel to be present (determination of a location for the maximum Quality Score) if the Quality Score exceeds a pre-defined threshold determined empirically from example images to achieve a desired trade-off of false-positive and false-negative ellipse detections.

The B-mode tracker (505-1 and 505-3) may be used by the algorithm to prescribe a search range for the ellipse parameters used to locate a vessel in the next image frame. For center location (x, y) of a given vessel location, the B-mode tracker predicts a search window based on the current vessel location and motion vector, in the same fashion as would be predicted by the Doppler tracker. This search window may be adjusted in size by the algorithm to speed up the search process when the algorithm determines that the vessel is overly compressed (for example, the aspect ratio being less than 0.2). The tracker also monitors whether the search for a vessel seed is going outside the boundaries of the predicted search window or the boundaries of the image. If so, the tracking of the seed (either B-mode or Doppler) may be terminated by the algorithm.

For the ellipse parameters (such as locations on the ellipse), a small interval centered on the current value of each parameter may be used by the algorithm as the search range. For example, the search interval for the long-axis radius may be given as [r0−dr, r0+dr], where r0 is the current radius value, and dr is a small increment, e.g., 8 pixels; the search interval for the aspect ratio may be given as [f0−df, f0+df], where f0 is the current aspect ratio value, and df is a small increment, e.g., 0.1; the search interval for the aspect ratio may be given as [f−df, f0+df], where f0 is the current aspect ratio value, and df is a small increment, e.g., 0.1. To accommodate the situation of a sudden change in vessel shape when vessel compression is applied by the user via the probe, these search intervals may be adjusted by the algorithm in size accordingly when a vessel is overly compressed.

Vein-artery discrimination may be performed by the algorithm at operation 506. Arterial flow is generally pulsatile, with periodicity corresponding to that of the heart rate of a subject of the ultrasound. Venous flow is generally phasic, with slower variations that are related more closely to respiration. Therefore, veins and arteries may be distinguished by the algorithm via the difference in temporal behavior of the flow magnitude.

Pulsatility estimate may be performed by the algorithm at operation 506-1. For a time series of flow scores for the seeds being tracked by the Doppler Tracker, a computation may be performed to measure a signature of pulsatility for each seed, as evidence for determining whether the location corresponds to a vein or artery. The pulsatility may be analyzed in several ways: 1) a simple pulsatility index may be computed by the algorithm, such as PI=(max (v)−min (v))/mean (v), where v represents the time series of the available flow scores from a time window leading up to the present moment, 2) a pulsatility score may be computed by the algorithm by detecting the periodicity of the autocorrelation of v (using any standard method for such detection), or 3) a pulsatility score may be computed by the algorithm by applying a machine learning classifier directly to v. By thresholding the pulsatility scores, a determination of whether or not a given vessel is pulsatile may be made, which is used to set the state of the Pulsatile indictor light shown in the user interface. This determination also informs the vein-artery discrimination in 506-3.

Compute distances between every pair of vessels may be performed by the algorithm at operation 506-2. In situations, such placement of PICC lines, where the spatial relationships of the vessels are fairly consistent across patients, the distance of a vessel relative to others provides a signature as to its identity. For example, no arteries are generally seen in the lateral aspect of the upper arm, and only one artery (the brachial artery) is seen in the medial aspect of the upper arm. Therefore, any major vessel seen in the lateral aspect is likely a vein. If it is near the skin surface, it is likely the cephalic vein; if it is deep, it is likely the ulnar vein. In the medial aspect, the brachial artery is immediately adjacent to various brachial veins, whereas the basilic vein is some distance away from this grouping. Thus, a vein that is reasonably well separated from an artery is most likely a vein (in particular, the basilic vein). Similarly, vessels immediately adjacent to an artery are most likely veins (in particular, brachial vein). Thus, by measuring the distances between vessels detected in the B-mode images, one can infer information that can contribute to vein-artery discrimination. Indeed, each vessel may be specifically named in some cases by the algorithm on the UI.

Updating a vein-artery flag for every vessel in vessel inventory may be performed by the algorithm at operation 506-3. Using a voting scheme based on the pulsatility score from Operation 506-1 and the distance measurements defined by the algorithm at operation 506-2, each vessel may be identified as either a vein or artery for purposes of defining the color coding shown in the user interface.

At operation UI image display 506', the method may, by way of operation 506'-1, display the B-mode image, and by way of operation 506'-2, display every vessel boundary overlay on the B-mode image, for example using red for artery and blue for vein.

Final analysis may be performed by the algorithm at operation 507.

Computation of compressibility index may be performed by the algorithm at operation 507-1, which may be calculated as a ratio (or difference) of maximum and minimum aspect ratios of the vessel during the compression phase of the ultrasound exam, or other similar measures of the variation in shape. If it is observed by the algorithm that the Quality Score drops below a preset threshold, indicating that the vessel effectively disappears from the B-mode image, this may be indicative of full compression.

Computation of a final value of pulsatility index may be computed by the algorithm at operation 507-2 based on an exam phase following a "Center the Vein" instruction by the algorithm to the user by way of the UI at operation 508. The anterior-posterior (AP) diameter of the vessel is obtained by the algorithm at operation 507-3 simply as the vertical dimension of the fitted ellipse. Vein depth is computed by the algorithm at operation 507-4 by measuring the distance in units of pixels from the top of the vein to the skin surface and converting to units of mm based on the known calibration scale of the image. Catheter gauge and French size may be determined by the algorithm at operation 507-5 and are based on AP diameter using known reference values.

Referring to operations 508, the algorithm may determine at operation 508-0 whether vessel compression is complete. If yes, the algorithm moves to operation 508-1, where it indicates to the user via the UI that the compression is complete, and if no, the algorithm moves to operation 508-3, where it determines whether a vein is centered in the image frame. If yes, the algorithm moves to operation 508-3, where it indicates to the user via the UI to compress the vein three times (or any number of times) for example using the probe, and if no, the algorithm moves to operation 508-4, where it determines whether there is a vein in the vessel inventory. If yes, the algorithm moves to operation 508-5, where it indicates to the user via the UI to center the vein, and if no, the algorithm moves to operation 508-6, where it determines whether a vein is centered in the image frame. If yes, the algorithm moves to operation 508-7, where it indicates to the user via the UI to locate the vein using the probe, and if no, the algorithm moves to operation 508-8, where it indicates to the user via the UI to place the probe. After the probe is placed, the method may move back to initialization at operation 501. After operations 508-1, 508-3, 508-5 and 508-7, the method may move back to operation 504.

Indicator lights on the user interface are set by the algorithm at operation 509 as follows. A Venous Flow light may be set by way of example to red (not venous) or green (venous) by comparison of the pulsatility index to a pre-defined threshold value chosen for desired trade-off of true-positive and false-positive determination within the range of the pulsatility index (for example, 0.5). Compressibility light is set similarly based on compressibility index. Sufficient Diameter light may be set comparing AP Diameter to known reference threshold used in clinical practice, with for example yellow indicating that the AP diameter is within some pre-defined range centered at the threshold, green indicating that the AP Diameter is above this range, and red indicating that the AP Diameter is below this range. Suitability for Access light may be for example set to red (not suitable) if any of the Venous Flow, Compressibility or Sufficient Diameter lights is set to red. If Venous Flow and Compressibility are set to green, then the status of the Suitability for Access light (determined by the algorithm at operation 507-6) is set the same as the Sufficient Diameter light.

Although the above description of exemplary embodiments may specifically mention veins, embodiments are not so limited, and pertain to the detection and tracking of any vessels with a body that may be the subject of ultrasonic imaging where the vessel is to be accessed by a foreign object. In addition, although certain colors are mentioned above to indicate suitability for access or other parameters relating to a vessel, embodiments are not so limited, and include within their scope an indication of vessel parameters to a user through a UI in any manner, such as through text, visual images or codes, voice communication.

In an example, instructions implemented by processor 326 may be provided via the memory 336 or any other memory or storage device of the imaging device, or the processor 326 or any other processor of the imaging device, may be embodied as a tangible, non-transitory, machine-readable medium including code to direct the processor 326 to perform electronic operations in the casing. The processor 326 may access the non-transitory, machine-readable medium over the an interconnect between memory 336 and processor 326. For instance, the non-transitory, machine-readable medium may be embodied by memory 336 or a separate memory within processor 326, or may include specific storage units such as optical disks, flash drives, or any number of other hardware devices that may be plugged into the casing. The non-transitory, machine-readable medium may include instructions to direct the processor 326 to perform a specific sequence or flow of actions, for example, as described with respect to the flowchart(s) and block diagram(s) of operations and functionality depicted herein. As used herein, the terms "machine-readable medium" and "computer-readable medium" are interchangeable.

Figure 6:
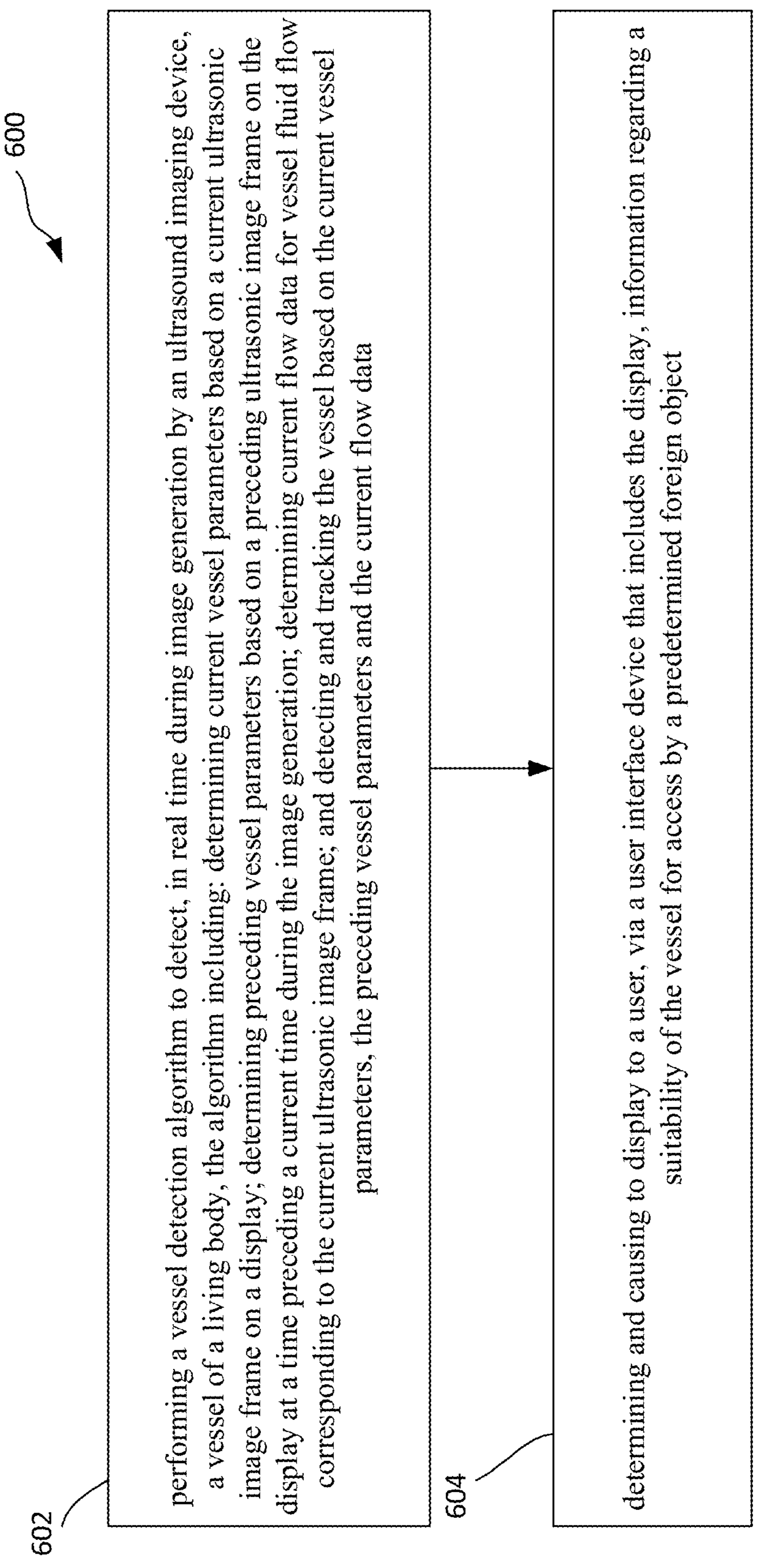
FIG. 6 depicts a flowchart of a process according to some embodiment.

FIG. 6 illustrates a method 600 to be performed at a computing device comprising a memory, and one or more processors coupled to the memory. Method 600 at operation 602 includes performing a vessel detection algorithm to detect, in real time during image generation by an ultrasound imaging device, a vessel of a living body, the algorithm including: determining current vessel parameters based on a current ultrasonic image frame on a display; determining preceding vessel parameters based on a preceding ultrasonic image frame on the display at a time preceding a current time during the image generation; determining current flow data for vessel fluid flow corresponding to the current ultrasonic image frame; and detecting and tracking the vessel based on the current vessel parameters, the preceding vessel parameters and the current flow data. The method at operation 604 includes determining and causing to display to a user, via a user interface device that includes the display, information regarding a suitability of the vessel for access by a predetermined foreign object.

Any of the below-described examples may be combined with any other example (or combination of examples), unless explicitly stated otherwise. Aspects described herein can also implement a hierarchical application of the scheme for example, by introducing a hierarchical prioritization of usage for different functions (e.g., low/medium/high priority, etc.).

Although implementations have been described with reference to specific exemplary aspects, it will be evident that various modifications and changes may be made to these aspects without departing from the broader scope of the present disclosure. Many of the arrangements and processes described herein can be used in combination or in parallel implementations. Accordingly, the specification and drawings are to be regarded in an illustrative rather than a restrictive sense. The accompanying drawings that form a part hereof show, by way of illustration, and not of limitation, specific aspects in which the subject matter may be practiced. The aspects illustrated are described in sufficient detail to enable those skilled in the art to practice the teachings disclosed herein. Other aspects may be utilized and derived therefrom, such that structural and logical substitutions and changes may be made without departing from the scope of this disclosure. This Detailed Description, therefore, is not to be taken in a limiting sense, and the scope of various aspects is defined only by the appended claims, along with the full range of equivalents to which such claims are entitled.

Such aspects of the inventive subject matter may be referred to herein, individually and/or collectively, merely for convenience and without intending to voluntarily limit the scope of this application to any single aspect or inventive concept if more than one is in fact disclosed.

While preferred embodiments of the present disclosure have been shown and described herein, it will be obvious to those skilled in the art that such embodiments are provided by way of example only. It is not intended that embodiments be limited by the specific examples provided within the specification. While embodiments of the disclosure have been described with reference to the aforementioned specification, the descriptions and illustrations of the embodiments herein are not meant to be construed in a limiting sense. Numerous variations, changes, and substitutions will now occur to those skilled in the art without departing from the concepts of the present disclosure. Furthermore, it shall be understood that all aspects of the various embodiments are not limited to the specific depictions, configurations, or relative proportions set forth herein, which depend upon a variety of conditions and variables. It should be understood that various alternatives to the embodiments described herein may be employed. It is therefore contemplated that the disclosure also covers any such alternatives, modifications, variations or equivalents.

EXAMPLES

Illustrative examples of the technologies disclosed herein are provided below. An embodiment of the technologies may include any one or more, and any combination of, the examples described below.

Example 1 includes an apparatus of a computing device comprising a memory, and one or more processors coupled to the memory to: perform a vessel detection algorithm to detect, in real time during image generation by an ultrasound imaging device, a vessel of a living body, the algorithm including: determining current vessel parameters based on a current ultrasonic image frame on a display at a current time; determining preceding vessel parameters based on a preceding ultrasonic image frame on the display at a time preceding the current time; determining current flow data for vessel fluid flow corresponding to the current ultrasonic image frame; and detecting and tracking the vessel based on the current vessel parameters, the preceding vessel parameters and the current flow data; and determine and cause to display to a user, via a user interface device that includes the display, information regarding a suitability of the vessel for access by a predetermined foreign object.

Example 2 includes the subject matter of Example 1, wherein the current flow data corresponds to current Doppler flow data, and the ultrasonic image is a two-dimensional ultrasonic image.

Example 3 includes the subject matter of Example 1, wherein the one or more processors are to select between determining the current flow data for a same field of view as the current ultrasonic image frame, and determining the current flow data for a smaller field of view than the same field of view.

Example 4 includes the subject matter of Example 3, wherein the one or more processors are to select to determine the current flow data for the same field of view at a start of image generation, and to subsequently select to determine the current flow data for the smaller field of view.

Example 5 includes the subject matter of Example 4, wherein the smaller field of view includes a predetermined number of image pixels to a at least one of a left, right, bottom or top edge of the same field of view.

Example 6 includes the subject matter of Example 1, wherein the one or more processors are to further cause the user interface device to communicate to the user information on the current flow data in real time during the image generation.

Example 7 includes the subject matter of Example 1, wherein the one or more processors are to further determine and cause to display to the user, via the user interface device, information regarding the current vessel parameters.

Example 8 includes the subject matter of Example 7, wherein the information regarding the current vessel parameters includes an outline of a boundary of the vessel and at least one of a location of its center or its diameter on the current ultrasonic image frame.

Example 9 includes the subject matter of Example 1, wherein the one or more processors are to cause to display to the user the information regarding the suitability of the vessel for access by the predetermined foreign object during performance of the vessel detection algorithm.

Example 10 includes the subject matter of Example 1, wherein the one or more processors are to determine a type of the predetermined foreign object by receiving signals from the user interface device corresponding to a selection of the type of the predetermined foreign object by the user.

Example 11 includes the subject matter of Example 1, wherein the one or more processors are to: access the memory to read information therefrom including a correlation between one or more of the vessel parameters with one or more attributes of the predetermined foreign object; and cause to communicate to the user, via the user interface device, information regarding the one or more attributes of the predetermined foreign object.

Example 12 includes the subject matter of any one of Examples 1-11, wherein the vessel parameters include one or more of a vessel dimension, vessel fluid flow rate, vessel pulsatility, vessel compressibility, or vessel outline.

Example 13 includes the subject matter of any one of Examples 1-11, wherein determining current vessel parameters includes identifying a candidate vessel seed location to be searched to detect the vessel by identifying a predetermined shape in the current ultrasonic image frame and by determining the candidate vessel seed location based on a location of the predetermined shape, the one or more processors to further analyze the candidate vessel seed location to detect the vessel by determining the current flow data corresponding to the candidate vessel seed location.

Example 14 includes the subject matter of Example 1, wherein the one or more processors include identifying a candidate vessel seed location to be searched to detect the vessel by identifying vessel fluid flow corresponding to the current ultrasonic image frame and by determining the candidate vessel seed location based on a location of the vessel fluid flow, the one or more processors to further analyze the candidate vessel seed location to detect the vessel by determining the current vessel parameters and determining the preceding vessel parameters at the candidate vessel seed location.

Example 15 includes the subject matter of Example 14, wherein determining the preceding vessel parameters includes using a preceding vessel quality score, the one or more processors to: determine the preceding vessel quality score by: determining a vessel boundary in the preceding ultrasonic image frame; and determining a strength of an image gradient averaged over a set of N points at the vessel boundary; and detect the vessel based on a determination that the preceding vessel quality score exceeds a predefined quality score threshold.

Example 16 includes the subject matter of Example 1, wherein the one or more processors are to perform the tracking algorithm by: using the preceding vessel parameters to determine a candidate vessel seed location to be tracked in a time domain to detect the vessel; generating a prediction of the current vessel parameters based on the preceding vessel parameters; and detecting the vessel based on a determination that a correlation exists between the current vessel parameters and the prediction.

Example 17 includes the subject matter of Example 16, wherein using the preceding vessel parameters includes using a preceding vessel quality score, the one or more processors to: determine the preceding vessel quality score by: determining a preceding vessel boundary in the preceding ultrasonic image frame; and determining a strength of an image gradient averaged over a set of N points at the preceding vessel boundary; and in response to a determination that the preceding vessel quality score exceeds a predefined quality score threshold, identify a location of the vessel boundary as the candidate vessel seed location.

Example 18 includes the subject matter of Example 17, wherein determining the current vessel parameters includes using a current vessel quality score, the one or more processors to: determine the current vessel quality score by: determining a current vessel boundary in the current ultrasonic image frame; and determining a strength of an image gradient averaged over a set of N points at the current vessel boundary; and in response to a determination that the current vessel quality score is below the predefined quality score threshold, determining the current flow data.

Example 19 includes the subject matter of Example 1, wherein the one or more processors are to perform the tracking algorithm by: using preceding flow data based on the preceding ultrasonic image frame to determine a candidate vessel seed location to be tracked in a time domain to detect the vessel; generating a prediction of the current flow data based on the preceding vessel parameters; and detecting the vessel based on a determination that a correlation exists between the current flow data and the prediction.

Example 20 includes the subject matter of any one of Examples 14-19, the one or more processors to cause to be stored in the memory a list of candidate vessel seed locations corresponding to the image generation, and of maximum flow amplitudes for respective ones of the candidate vessel seed locations, wherein determining the current flow data includes determining a respective plurality of current flow data corresponding to at least some of respective ones of the candidate vessel seed locations.

Example 21 includes the subject matter of any one of Examples 16-18, wherein the one or more processors are to perform the tracking algorithm by jointly analyzing a plurality of preceding ultrasonic image frames to detect the vessel in the current ultrasonic image frame, jointly analyzing including one of using a multichannel implementation of a You Only Look Once (YOLO) algorithm, or using an algorithm including a combined convolutional neural network and long short-term memory network.

Example 22 includes the subject matter of Example 1, wherein the one or more processors are further to identify whether the vessel corresponds to a vein or to an artery by determining at least one of a compressibility of the vessel, or a pulsatility of the vessel based on analyzing a periodic behavior of flow within the vessel.

Example 23 includes the subject matter of Example 22, wherein the one or more processors are to identify whether the vessel corresponds to a vein or to an artery by further computing a distance between pairs of vessels in the current image frame.

Example 24 includes the subject matter of Example 22, wherein the one or more processors are to determine the pulsatility by analyzing data on spatial movements in proximity to the vessel as between successive ultrasonic image frames, or by performing a local analysis of a motion of walls of the vessel.

Example 25 includes the subject matter of Example 1, wherein the one or more processors are to determine at least one of the current vessel parameters or the preceding vessel parameters by using a spatial search range based on a compression level of the vessel.

Example 26 includes a system including; a user interface device including a display device; and a computing device communicatively coupled to the user interface device, the computing device comprising a memory, and one or more processors coupled to the memory to: perform a vessel detection algorithm to detect, in real time during image generation by an ultrasound imaging device, a vessel of a living body, the algorithm including: determining current vessel parameters based on a current ultrasonic image frame on the display; determining preceding vessel parameters based on a preceding ultrasonic image frame on the display at a time preceding a current time during the image generation; determining current flow data for vessel fluid flow corresponding to the current ultrasonic image frame; and detecting and tracking the vessel based on the current vessel parameters, the preceding vessel parameters and the current flow data; and determine and cause to display to a user, via the user interface device, information regarding a suitability of the vessel for access by a predetermined foreign object.

Example 27 includes the subject matter of Example 26, wherein the current flow data corresponds to current Doppler flow data, and the ultrasonic image is a two-dimensional ultrasonic image.

Example 28 includes the subject matter of Example 26, wherein the one or more processors are to select between determining the current flow data for a same field of view as the current ultrasonic image frame, and determining the current flow data for a smaller field of view than the same field of view.

Example 29 includes the subject matter of Example 28, wherein the one or more processors are to select to determine the current flow data for the same field of view at a start of image generation, and to subsequently select to determine the current flow data for the smaller field of view.

Example 30 includes the subject matter of Example 29, wherein the smaller field of view includes a predetermined number of image pixels to a at least one of a left, right, bottom or top edge of the same field of view.

Example 31 includes the subject matter of Example 26, wherein the one or more processors are to further cause the user interface device to communicate to the user information on the current flow data in real time during the image generation.

Example 32 includes the subject matter of Example 26, wherein the one or more processors are to further determine and cause to display to the user, via the user interface device, information regarding the current vessel parameters.

Example 33 includes the subject matter of Example 32, wherein the information regarding the current vessel parameters includes an outline of a boundary of the vessel and at least one of a location of its center or its diameter on the current ultrasonic image frame.

Example 34 includes the subject matter of Example 26, wherein the one or more processors are to cause to display to the user the information regarding the suitability of the vessel for access by the predetermined foreign object during performance of the vessel detection algorithm.

Example 35 includes the subject matter of Example 26, wherein the one or more processors are to determine a type of the predetermined foreign object by receiving signals from the user interface device corresponding to a selection of the type of the predetermined foreign object by the user.

Example 36 includes the subject matter of Example 26, wherein the one or more processors are to: access the memory to read information therefrom including a correlation between one or more of the vessel parameters with one or more attributes of the predetermined foreign object; and cause to communicate to the user, via the user interface device, information regarding the one or more attributes of the predetermined foreign object.

Example 37 includes the subject matter of any one of Examples 26-36, wherein the vessel parameters include one or more of a vessel dimension, vessel fluid flow rate, vessel pulsatility, vessel compressibility, or vessel outline.

Example 38 includes the subject matter of any one of Examples 26-36, wherein determining current vessel parameters includes identifying a candidate vessel seed location to be searched to detect the vessel by identifying a predetermined shape in the current ultrasonic image frame and by determining the candidate vessel seed location based on a location of the predetermined shape, the one or more processors to further analyze the candidate vessel seed location to detect the vessel by determining the current flow data corresponding to the candidate vessel seed location.

Example 39 includes the subject matter of Example 26, wherein the one or more processors include identifying a candidate vessel seed location to be searched to detect the vessel by identifying vessel fluid flow corresponding to the current ultrasonic image frame and by determining the candidate vessel seed location based on a location of the vessel fluid flow, the one or more processors to further analyze the candidate vessel seed location to detect the vessel by determining the current vessel parameters and determining the preceding vessel parameters at the candidate vessel seed location.

Example 40 includes the subject matter of Example 39, wherein determining the preceding vessel parameters includes using a preceding vessel quality score, the one or more processors to: determine the preceding vessel quality score by: determining a vessel boundary in the preceding ultrasonic image frame; and determining a strength of an image gradient averaged over a set of N points at the vessel boundary; and detect the vessel based on a determination that the preceding vessel quality score exceeds a predefined quality score threshold.

Example 41 includes the subject matter of Example 26, wherein the one or more processors are to perform the tracking algorithm by: using the preceding vessel parameters to determine a candidate vessel seed location to be tracked in a time domain to detect the vessel; generating a prediction of the current vessel parameters based on the preceding vessel parameters; and detecting the vessel based on a determination that a correlation exists between the current vessel parameters and the prediction.

Example 42 includes the subject matter of Example 41, wherein using the preceding vessel parameters includes using a preceding vessel quality score, the one or more processors to: determine the preceding vessel quality score by: determining a preceding vessel boundary in the preceding ultrasonic image frame; and determining a strength of an image gradient averaged over a set of N points at the preceding vessel boundary; and in response to a determination that the preceding vessel quality score exceeds a predefined quality score threshold, identify a location of the vessel boundary as the candidate vessel seed location.

Example 43 includes the subject matter of Example 42, wherein determining the current vessel parameters includes using a current vessel quality score, the one or more processors to: determine the current vessel quality score by: determining a current vessel boundary in the current ultrasonic image frame; and determining a strength of an image gradient averaged over a set of N points at the current vessel boundary; and in response to a determination that the current vessel quality score is below the predefined quality score threshold, determining the current flow data.

Example 44 includes the subject matter of Example 26, wherein the one or more processors are to perform the tracking algorithm by: using preceding flow data based on the preceding ultrasonic image frame to determine a candidate vessel seed location to be tracked in a time domain to detect the vessel; generating a prediction of the current flow data based on the preceding vessel parameters; and detecting the vessel based on a determination that a correlation exists between the current flow data and the prediction.

Example 45 includes the subject matter of any one of Examples 39-44, the one or more processors to cause to be stored in the memory a list of candidate vessel seed locations corresponding to the image generation, and of maximum flow amplitudes for respective ones of the candidate vessel seed locations, wherein determining the current flow data includes determining a respective plurality of current flow data corresponding to at least some of respective ones of the candidate vessel seed locations.

Example 46 includes the subject matter of any one of Examples 41-43, wherein the one or more processors are to perform the tracking algorithm by jointly analyzing a plurality of preceding ultrasonic image frames to detect the vessel in the current ultrasonic image frame, jointly analyzing including one of using a multichannel implementation of a You Only Look Once (YOLO) algorithm, or using an algorithm including a combined convolutional neural network and long short-term memory network.

Example 47 includes the subject matter of Example 26, wherein the one or more processors are further to identify whether the vessel corresponds to a vein or to an artery by determining at least one of a compressibility of the vessel, or a pulsatility of the vessel based on analyzing a periodic behavior of flow within the vessel.

Example 48 includes the subject matter of Example 47, wherein the one or more processors are to identify whether the vessel corresponds to a vein or to an artery by further computing a distance between pairs of vessels in the current image frame.

Example 49 includes the subject matter of Example 47, wherein the one or more processors are to determine the pulsatility by analyzing data on spatial movements in proximity to the vessel as between successive ultrasonic image frames, or by performing a local analysis of a motion of walls of the vessel.

Example 50 includes the subject matter of Example 26, wherein the one or more processors are to determine at least one of the current vessel parameters or the preceding vessel parameters by using a spatial search range based on a compression level of the vessel.

Example 51 includes a method to be performed at a computing device comprising a memory, and one or more processors coupled to the memory, the method including: performing a vessel detection algorithm to detect, in real time during image generation by an ultrasound imaging device, a vessel of a living body, the algorithm including: determining current vessel parameters based on a current ultrasonic image frame on a display; determining preceding vessel parameters based on a preceding ultrasonic image frame on the display at a time preceding a current time during the image generation; determining current flow data for vessel fluid flow corresponding to the current ultrasonic image frame; and detecting and tracking the vessel based on the current vessel parameters, the preceding vessel parameters and the current flow data; and determining and causing to display to a user, via a user interface device that includes the display, information regarding a suitability of the vessel for access by a predetermined foreign object.

Example 52 includes the subject matter of Example 51, wherein the current flow data corresponds to current Doppler flow data, and the ultrasonic image is a two-dimensional ultrasonic image.

Example 53 includes the subject matter of Example 51, the method further including selecting between determining the current flow data for a same field of view as the current ultrasonic image frame, and determining the current flow data for a smaller field of view than the same field of view.

Example 54 includes the subject matter of Example 53, the method further including selecting to determine the current flow data for the same field of view at a start of an image generation, and subsequently selecting to determine the current flow data for the smaller field of view.

Example 55 includes the subject matter of Example 54, wherein the smaller field of view includes a predetermined number of image pixels to a at least one of a left, right, bottom or top edge of the same field of view.

Example 56 includes the subject matter of Example 51, the method further including causing the user interface device to communicate to the user information on the current flow data in real time during the image generation.

Example 57 includes the subject matter of Example 51, the method further including determining and causing to display to the user, via the user interface device, information regarding the current vessel parameters.

Example 58 includes the subject matter of Example 57, wherein the information regarding the current vessel parameters includes an outline of a boundary of the vessel and at least one of a location of its center or its diameter on the current ultrasonic image frame.

Example 59 includes the subject matter of Example 51, the method further including causing to display to the user the information regarding the suitability of the vessel for access by the predetermined foreign object during performance of the vessel detection algorithm.

Example 60 includes the subject matter of Example 51, the method further including determining a type of the predetermined foreign object by receiving signals from the user interface device corresponding to a selection of the type of the predetermined foreign object by the user.

Example 61 includes the subject matter of Example 51, the method further including: accessing the memory to read information therefrom including a correlation between one or more of the vessel parameters with one or more attributes of the predetermined foreign object; and causing to communicate to the user, via the user interface device, information regarding the one or more attributes of the predetermined foreign object.

Example 62 includes the subject matter of any one of Examples 51-61, wherein the vessel parameters include one or more of a vessel dimension, vessel fluid flow rate, vessel pulsatility, vessel compressibility, or vessel outline.

Example 63 includes the subject matter of any one of Examples 51-61, wherein determining current vessel parameters includes identifying a candidate vessel seed location to be searched to detect the vessel by identifying a predetermined shape in the current ultrasonic image frame and by determining the candidate vessel seed location based on a location of the predetermined shape, the method further including analyzing the candidate vessel seed location to detect the vessel by determining the current flow data corresponding to the candidate vessel seed location.

Example 64 includes the subject matter of Example 51, the method including identifying a candidate vessel seed location to be searched to detect the vessel by identifying vessel fluid flow corresponding to the current ultrasonic image frame and by determining the candidate vessel seed location based on a location of the vessel fluid flow, the method further including analyzing the candidate vessel seed location to detect the vessel by determining the current vessel parameters and determining the preceding vessel parameters at the candidate vessel seed location.

Example 65 includes the subject matter of Example 64, wherein determining the preceding vessel parameters includes using a preceding vessel quality score, the method further including: determining the preceding vessel quality score by: determining a vessel boundary in the preceding ultrasonic image frame; and determining a strength of an image gradient averaged over a set of N points at the vessel boundary; and detecting the vessel based on a determination that the preceding vessel quality score exceeds a predefined quality score threshold.

Example 66 includes the subject matter of Example 51, the method further including performing the tracking algorithm by: using the preceding vessel parameters to determine a candidate vessel seed location to be tracked in a time domain to detect the vessel; generating a prediction of the current vessel parameters based on the preceding vessel parameters; and detecting the vessel based on a determination that a correlation exists between the current vessel parameters and the prediction.

Example 67 includes the subject matter of Example 66, wherein using the preceding vessel parameters includes using a preceding vessel quality score, the method including: determining the preceding vessel quality score by: determining a preceding vessel boundary in the preceding ultrasonic image frame; and determining a strength of an image gradient averaged over a set of N points at the preceding vessel boundary; and in response to a determination that the preceding vessel quality score exceeds a predefined quality score threshold, identifying a location of the vessel boundary as the candidate vessel seed location.

Example 68 includes the subject matter of Example 67, wherein determining the current vessel parameters includes using a current vessel quality score, the method further including: determining the current vessel quality score by: determining a current vessel boundary in the current ultrasonic image frame; and determining a strength of an image gradient averaged over a set of N points at the current vessel boundary; and in response to a determination that the current vessel quality score is below the predefined quality score threshold, determining the current flow data.

Example 69 includes the subject matter of Example 51, the method further including performing the tracking algorithm by: using preceding flow data based on the preceding ultrasonic image frame to determine a candidate vessel seed location to be tracked in a time domain to detect the vessel; generating a prediction of the current flow data based on the preceding vessel parameters; and detecting the vessel based on a determination that a correlation exists between the current flow data and the prediction.

Example 70 includes the subject matter of any one of Examples 64-69, the method including causing to be stored in the memory a list of candidate vessel seed locations corresponding to the image generation, and of maximum flow amplitudes for respective ones of the candidate vessel seed locations, wherein determining the current flow data includes determining a respective plurality of current flow data corresponding to at least some of respective ones of the candidate vessel seed locations.

Example 71 includes the subject matter of any one of Examples 66-68, the method further including performing the tracking algorithm by jointly analyzing a plurality of preceding ultrasonic image frames to detect the vessel in the current ultrasonic image frame, jointly analyzing including one of using a multichannel implementation of a You Only Look Once (YOLO) algorithm, or using an algorithm including a combined convolutional neural network and long short-term memory network.

Example 72 includes the subject matter of Example 51, the method further including identifying whether the vessel corresponds to a vein or to an artery by determining at least one of a compressibility of the vessel, or a pulsatility of the vessel based on analyzing a periodic behavior of flow within the vessel.

Example 73 includes the subject matter of Example 72, the method further including identifying whether the vessel corresponds to a vein or to an artery by further computing a distance between pairs of vessels in the current image frame.

Example 74 includes the subject matter of Example 72, the method further including determining the pulsatility by analyzing data on spatial movements in proximity to the vessel as between successive ultrasonic image frames, or by performing a local analysis of a motion of walls of the vessel.

Example 75 includes the subject matter of Example 51, the method further including determining at least one of the current vessel parameters or the preceding vessel parameters by using a spatial search range based on a compression level of the vessel.

Example 76 includes an apparatus comprising means for performing the method of any one of Examples 51-75.

Example 77 includes one or more computer-readable media comprising a plurality of instructions stored thereon that, when executed, cause one or more processors to perform the method of any one of Examples 51-75.

Example 78 includes an imaging device comprising the apparatus of any one of Examples 1-25, and further including the user interface device.

Example 79 includes a product comprising one or more tangible computer-readable non-transitory storage media comprising computer-executable instructions operable to, when executed by at least one computer processor, enable the at least one processor to perform the method of any one of Examples 51-75.

What is claimed is:

1. An apparatus of a computing device comprising a memory, and one or more processors coupled to the memory to:

perform a vessel detection algorithm to detect, in real time during image generation by an ultrasound imaging device, a vessel of a living body, the vessel detection algorithm including:

determining current vessel parameters based on a current ultrasonic image frame on a display at a current time;

determining preceding vessel parameters based on a preceding ultrasonic image frame on the display at a time preceding the current time;

determining current flow data for vessel fluid flow corresponding to the current ultrasonic image frame; and detecting and tracking the vessel based on the current vessel parameters, the preceding vessel parameters and the current flow data; and determine and cause to display to a user, via a user interface device that includes the display, information regarding a suitability of the vessel for access by a predetermined foreign object, wherein the one or more processors are to:

access the memory to read information therefrom including a correlation between, on one hand, one or more attributes of the predetermined foreign object, and, on another hand, one or more of:

the current vessel parameters; or the preceding vessel parameters; and cause to communicate to the user, via the user interface device, information regarding the one or more attributes of the predetermined foreign object.

2. The apparatus of claim 1, wherein the current flow data corresponds to current Doppler flow data, and the ultrasonic image is a two-dimensional ultrasonic image.

3. The apparatus of claim 1, wherein the one or more processors are to select between determining the current flow data for a same field of view as the current ultrasonic image frame, and determining the current flow data for a smaller field of view than the same field of view.

4. The apparatus of claim 3, wherein the one or more processors are to select to determine the current flow data for the same field of view at a start of image generation, and to subsequently select to determine the current flow data for the smaller field of view.

5. The apparatus of claim 4, wherein the smaller field of view includes a predetermined number of image pixels to at least one of a left, right, bottom or top edge of the same field of view.

6. The apparatus of claim 1, wherein the one or more processors are to further cause the user interface device to communicate to the user information on the current flow data in real time during the image generation.

7. The apparatus of claim 1, wherein the one or more processors are to further determine and cause to display to the user, via the user interface device, information regarding the current vessel parameters.

8. The apparatus of claim 7, wherein the information regarding the current vessel parameters includes an outline of a boundary of the vessel and at least one of a location of its center or its diameter on the current ultrasonic image frame.

9. The apparatus of claim 1, wherein the one or more processors are to cause to display to the user the information regarding the suitability of the vessel for access by the predetermined foreign object during performance of the vessel detection algorithm.

10. The apparatus of claim 1, wherein the vessel parameters include one or more of a vessel dimension, vessel fluid flow rate, vessel pulsatility, vessel compressibility, or vessel outline.

11. The apparatus of claim 1, wherein determining current vessel parameters includes identifying a candidate vessel seed location to be searched to detect the vessel by identifying a predetermined shape in the current ultrasonic image frame and by determining the candidate vessel seed location based on a location of the predetermined shape, the one or more processors to further analyze the candidate vessel seed location to detect the vessel by determining the current flow data corresponding to the candidate vessel seed location.

12. A system including:

a user interface device including a display device; and a computing device communicatively coupled to the user interface device, the computing device comprising a memory, and one or more processors coupled to the memory to:

perform a vessel detection algorithm to detect, in real time during image generation by an ultrasound imaging device, a vessel of a living body, the vessel detection algorithm including:

determining current vessel parameters based on a current ultrasonic image frame on the display;

determining preceding vessel parameters based on a preceding ultrasonic image frame on the display at a time preceding a current time during the image generation;

determining current flow data for vessel fluid flow corresponding to the current ultrasonic image frame; and detecting and tracking the vessel based on the current vessel parameters, the preceding vessel parameters and the current flow data; and determine and cause to display to a user, via the user interface device, information regarding a suitability of the vessel for access by a predetermined foreign object;

identify a candidate vessel seed location to be searched to detect the vessel by identifying vessel fluid flow corresponding to the current ultrasonic image frame and by determining the candidate vessel seed location based on a location of the vessel fluid flow; and analyze the candidate vessel seed location to detect the vessel by determining the current vessel parameters and determining the preceding vessel parameters at the candidate vessel seed location.

13. The system of claim 12, wherein the vessel parameters include one or more of a vessel dimension, vessel fluid flow rate, vessel pulsatility, vessel compressibility, or vessel outline.

14. A method to be performed at a computing device comprising a memory, and one or more processors coupled to the memory, the method including:

performing a vessel detection algorithm to detect, in real time during image generation by an ultrasound imaging device, a vessel of a living body, the vessel detection algorithm including:

determining current vessel parameters based on a current ultrasonic image frame on a display;

determining preceding vessel parameters based on a preceding ultrasonic image frame on the display at a time preceding a current time during the image generation;

determining current flow data for vessel fluid flow corresponding to the current ultrasonic image frame; and detecting and tracking the vessel based on the current vessel parameters, the preceding vessel parameters and the current flow data;

determining and causing to display to a user, via a user interface device that includes the display, information regarding a suitability of the vessel for access by a predetermined foreign object; and identifying a candidate vessel seed location to be searched to detect the vessel by identifying vessel fluid flow corresponding to the current ultrasonic image frame and by determining the candidate vessel seed location based on a location of the vessel fluid flow, the method further including analyzing the candidate vessel seed location to detect the vessel by determining the current vessel parameters and determining the preceding vessel parameters at the candidate vessel seed location.

15. The method of claim 14, wherein determining the preceding vessel parameters includes using a preceding vessel quality score, the method further including:

determining the preceding vessel quality score by:

determining a vessel boundary in the preceding ultrasonic image frame; and determining a strength of an image gradient averaged over a set of N points at the vessel boundary; and detecting the vessel based on a determination that the preceding vessel quality score exceeds a predefined quality score threshold.

16. The method of claim 14, the method further including performing the vessel detection algorithm by:

using the preceding vessel parameters to determine a candidate vessel seed location to be tracked in a time domain to detect the vessel;

generating a prediction of the current vessel parameters based on the preceding vessel parameters; and detecting the vessel based on a determination that a correlation exists between the current vessel parameters and the prediction.

17. The method of claim 16, wherein using the preceding vessel parameters includes using a preceding vessel quality score, the method including:

determining the preceding vessel quality score by:

determining a preceding vessel boundary in the preceding ultrasonic image frame; and determining a strength of an image gradient averaged over a set of N points at the preceding vessel boundary; and in response to a determination that the preceding vessel quality score exceeds a predefined quality score threshold, identifying a location of the vessel boundary as the candidate vessel seed location.

18. One or more computer-readable media comprising a plurality of instructions stored thereon that, when executed, cause one or more processors to perform operations including:

performing a vessel detection algorithm to detect, in real time during image generation by an ultrasound imaging device, a vessel of a living body, the vessel detection algorithm including:

determining current vessel parameters based on a current ultrasonic image frame on a display;

determining preceding vessel parameters based on a preceding ultrasonic image frame on the display at a time preceding a current time during the image generation;

determining current flow data for vessel fluid flow corresponding to the current ultrasonic image frame; and detecting and tracking the vessel based on the current vessel parameters, the preceding vessel parameters and the current flow data;

determining and causing to display to a user, via a user interface device that includes the display, information regarding a suitability of the vessel for access by a predetermined foreign object, wherein determining the preceding vessel parameters includes using a preceding vessel quality score;

determining the preceding vessel quality score by:

determining a vessel boundary in the preceding ultrasonic image frame; and determining a strength of an image gradient averaged over a set of N points at the vessel boundary; and detecting the vessel based on a determination that the preceding vessel quality score exceeds a predefined quality score threshold.

19. The one or more computer-readable media of claim 18, the operations further including identifying a candidate vessel seed location to be searched to detect the vessel by identifying vessel fluid flow corresponding to the current ultrasonic image frame and by determining the candidate vessel seed location based on a location of the vessel fluid flow, the operations further including analyzing the candidate vessel seed location to detect the vessel by determining the current vessel parameters and determining the preceding vessel parameters at the candidate vessel seed location.

20. An apparatus of a computing device comprising:

means for performing a vessel detection algorithm to detect, in real time during image generation by an ultrasound imaging device, a vessel of a living body, the vessel detection algorithm including:

determining current vessel parameters based on a current ultrasonic image frame on a display;

determining preceding vessel parameters based on a preceding ultrasonic image frame on the display at a time preceding a current time during the image generation;

determining current flow data for vessel fluid flow corresponding to the current ultrasonic image frame; and detecting and tracking the vessel based on the current vessel parameters, the preceding vessel parameters and the current flow data; and means for determining information regarding a suitability of the vessel for access by a predetermined foreign object, wherein determining the preceding vessel parameters includes using a preceding vessel quality score;

means for determining the preceding vessel quality score by:

determining a vessel boundary in the preceding ultrasonic image frame; and determining a strength of an image gradient averaged over a set of N points at the vessel boundary; and means for detecting the vessel based on a determination that the preceding vessel quality score exceeds a predefined quality score threshold.

21. The apparatus of claim 20, further including means for identifying a candidate vessel seed location to be searched to detect the vessel by identifying vessel fluid flow corresponding to the current ultrasonic image frame and by determining the candidate vessel seed location based on a location of the vessel fluid flow, and means for analyzing the candidate vessel seed location to detect the vessel by determining the current vessel parameters and determining the preceding vessel parameters at the candidate vessel seed location.

22. The apparatus of claim 21, wherein determining the preceding vessel parameters includes using a preceding vessel quality score, the apparatus further including:

means for determining the preceding vessel quality score by:

determining a vessel boundary in the preceding ultrasonic image frame; and determining a strength of an image gradient averaged over a set of N points at the vessel boundary; and means for detecting the vessel based on a determination that the preceding vessel quality score exceeds a predefined quality score threshold.

* * * * *